(12) United States Patent
Nurse et al.

(10) Patent No.: US 7,765,719 B2
(45) Date of Patent: Aug. 3, 2010

(54) MEDIALLY OR LATERALLY TEXTURED FOOTBEDS FOR CONTROLLING LOWER EXTREMITY KINEMATICS AND KINETICS

(75) Inventors: Matthew Anthony Nurse, Lake Oswego, OR (US); Mario A. Lafortune, Tigard, OR (US)

(73) Assignee: NIKE, Inc., Beaverton, OR (US)

( * ) Notice: Subject to any disclaimer, the term of this patent is extended or adjusted under 35 U.S.C. 154(b) by 626 days.

(21) Appl. No.: 11/420,572

(22) Filed: May 26, 2006

(65) Prior Publication Data

US 2007/0271820 A1    Nov. 29, 2007

(51) Int. Cl.
*A43B 13/00* (2006.01)
*A43B 13/38* (2006.01)
(52) U.S. Cl. .............................. 36/25 R; 36/43; 36/144
(58) Field of Classification Search .................. 36/25 R, 36/43, 144, 44, 140, 141, 143
See application file for complete search history.

(56) References Cited

U.S. PATENT DOCUMENTS

| | | | |
|---|---|---|---|
| 2,139,971 A | 12/1938 | Pava | |
| 3,757,774 A | 9/1973 | Hatuno | |
| 4,020,570 A | 5/1977 | Shames | |
| 4,033,054 A | 7/1977 | Fukuoka | |
| 4,045,886 A * | 9/1977 | Terasaki | ........................ 36/44 |
| 4,047,310 A | 9/1977 | Sunoo | |
| 4,694,831 A | 9/1987 | Seltzer | |
| 4,760,655 A | 8/1988 | Mauch | |
| 4,841,647 A | 6/1989 | Turucz | |
| 5,551,173 A | 9/1996 | Chambers | |
| 5,564,989 A | 10/1996 | Larsen | |
| 5,664,342 A | 9/1997 | Bushsenschuss | |
| 6,301,805 B1 | 10/2001 | Howlett et al. | |
| 6,598,321 B2 | 7/2003 | Crane et al. | |
| 6,631,568 B2 | 10/2003 | Howlett et al. | |

(Continued)

FOREIGN PATENT DOCUMENTS

DE     20314683 U1    12/2003

(Continued)

OTHER PUBLICATIONS

International Search Report in corresponding PCT application, International Application No. PCT/US2007/010374, mailed Nov. 9, 2007.

(Continued)

*Primary Examiner*—Ted Kavanaugh
(74) *Attorney, Agent, or Firm*—Banner & Witcoff, Ltd.

(57) ABSTRACT

Footbeds (e.g., in footwear, socks, etc.) for engaging a plantar surface of a wearer's foot include one of the lateral or medial sides having a smooth or substantially smooth feel or surface while the opposite side has a textured feel or surface, e.g., by providing plural raised areas that define the textured feel or surface. Depending on the location of the texturing (lateral side or medial side) and/or the type of ambulatory activity (e.g., running or walking), lower extremity movement during the activity may be affected, e.g., to reduce pronation, reduce maximum eversion, reduce rearfoot range of motion, reduce eversion velocity, reduce plantarflexion when pushing off during a step, reduce inversion at heel strike, reduce eversion range of motion, reduce maximum internal tibial rotation, to increase stability during cutting motions, etc.

22 Claims, 20 Drawing Sheets

U.S. PATENT DOCUMENTS

| | | | |
|---|---|---|---|
| 6,715,221 B1 * | 4/2004 | Sasaki | 36/141 |
| 6,978,684 B2 | 12/2005 | Nurse | |
| 7,243,446 B2 | 7/2007 | Vindriis | |
| 2003/0177667 A1 * | 9/2003 | Hussain | 36/144 |
| 2004/0221371 A1 | 11/2004 | Kato | |

FOREIGN PATENT DOCUMENTS

| | | |
|---|---|---|
| EP | 0966891 A2 | 12/1999 |
| GB | 2296646 A | 7/1996 |
| WO | 2005004658 A1 | 1/2005 |

OTHER PUBLICATIONS

Internet Printout: http://www.insole.com/softsole.html, Sof Sole Product Page, dated Mar. 6, 2006.

Internet Printout: http://www.footinsoles.co.uk/pronation.htm—Over Pronation and Over Pronation Insoles, dated Mar. 6, 2006.

Internet Printout: http://www.footsmart.com/Product.aspx—Bio-Stride Insoles, Pair, dated Mar. 6, 2006.

Internet Printout: http://www.footsmart.com/Product.aspx—Bio Balance Anti-Pronation Insoles, Pair::Insoles::FootSmart dated Mar. 6, 2006.

Matthew A. Nurse et al., "Changing the texture of footwear can alter gait patterns", Journal of Electromyography and Kinesiology 15, pp. 496-506 (2005).

Matthew A. Nurse et al., "The effect of changes in foot sensation on plantar pressure and muscle activity", Clinical Biomechanics 16, pp. 719-727 (2001).

Benno M. Nigg et al., "Shoe inserts and orthotics for sport and physical activites", Medicine & Science in Sports & Exercise, vol. 31, No. 7, pp. S421-S428,1999.

International Preliminary Report on Patentability in corresponding PCT Application, International Application No. PCT/US2007/010374, mailed Dec. 11, 2008.

* cited by examiner

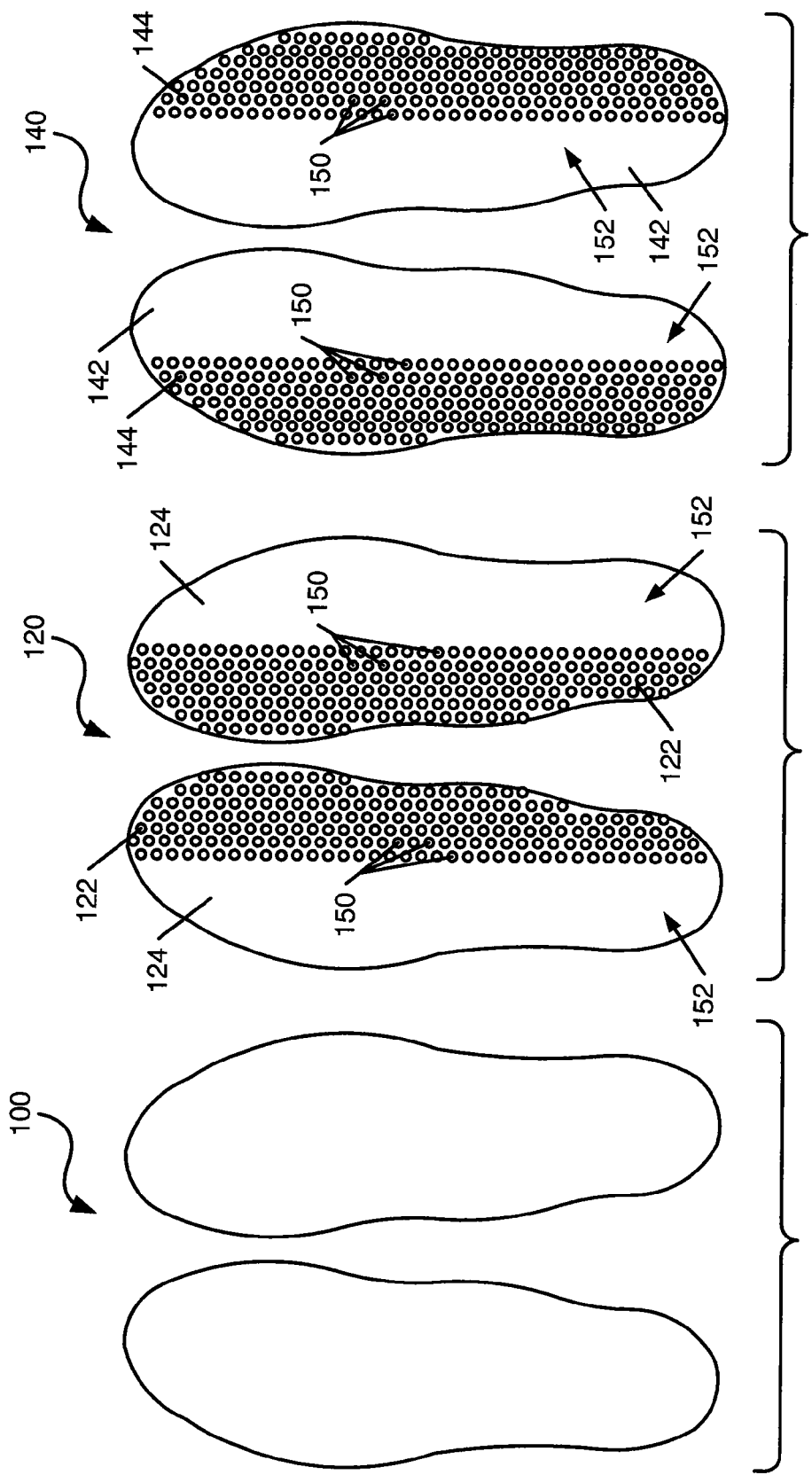

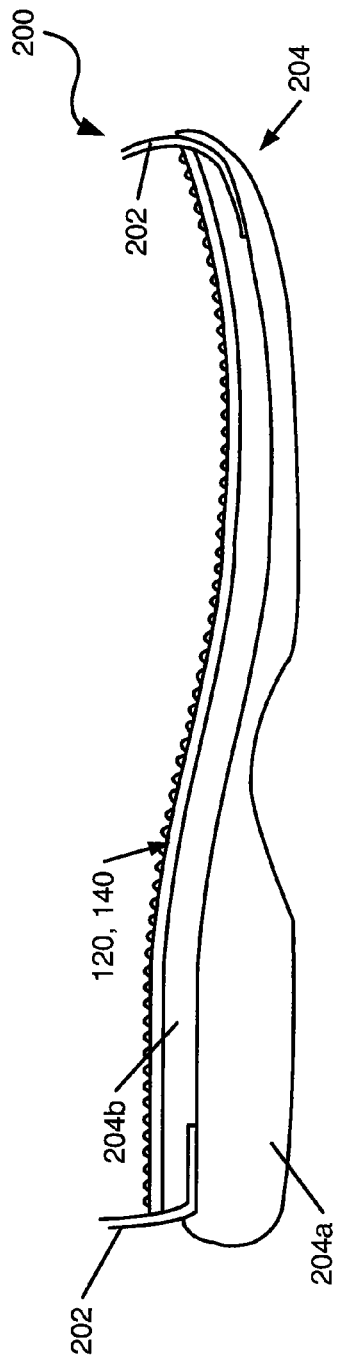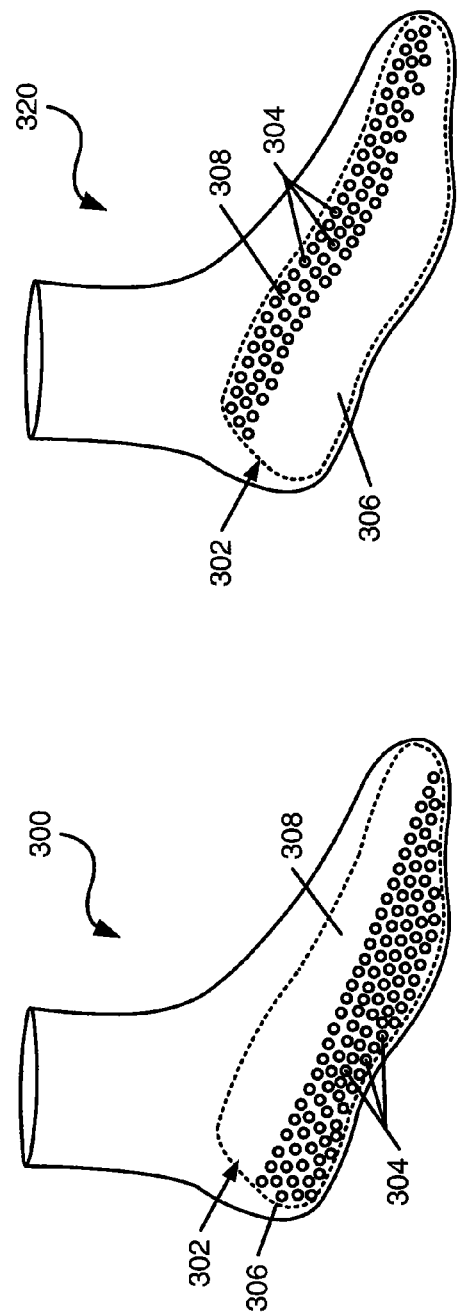

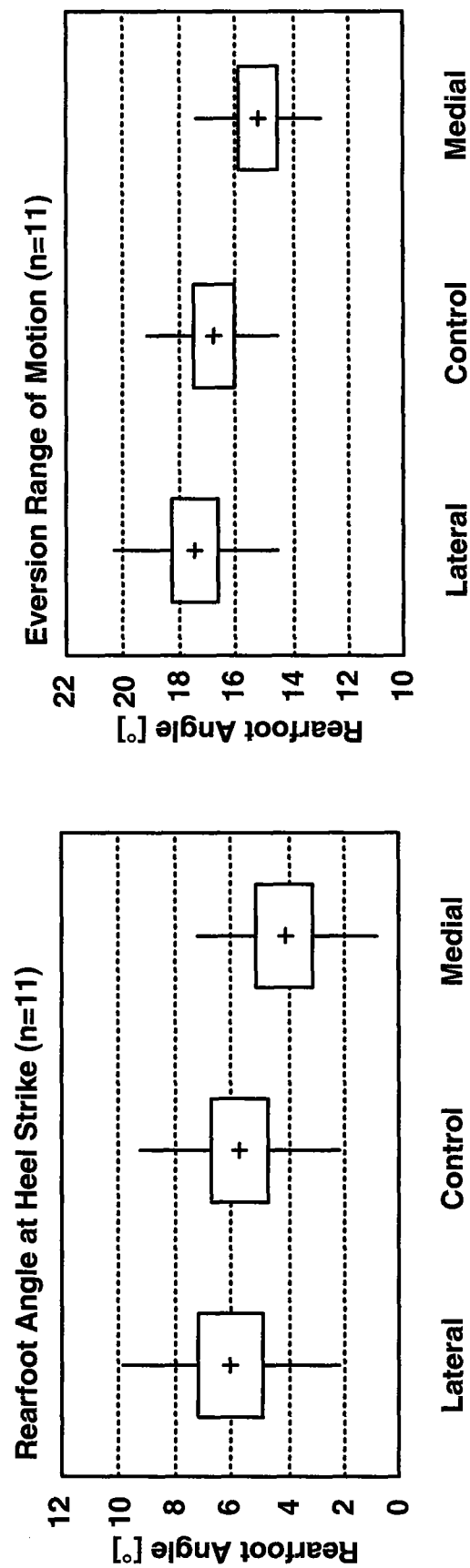

ized by the upper member and a sole structure. The upper member and a sole structure. The upper member may have a configuration that protects the foot and provides ventilation, thereby cooling the foot and removing perspiration. The sole structure generally is secured to a lower portion of the upper member and generally is positioned between the foot and a contact surface (which may include any foot or footwear contact surface, including but not limited to: ground, grass, dirt, sand, snow, ice, tile, flooring, carpeting, synthetic grass, artificial turf, and the like). In addition to attenuating contact surface reaction forces, the sole structure may provide traction and help control foot motion, such as pronation. Accordingly, the upper member and the sole structure operate cooperatively to provide a comfortable structure that is suited for a variety of ambulatory activities, such as walking and running.

MEDIALLY OR LATERALLY TEXTURED FOOTBEDS FOR CONTROLLING LOWER EXTREMITY KINEMATICS AND KINETICS

FIELD OF THE INVENTION

The present invention relates generally to products and methods for controlling lower extremity motion, e.g., by altering sensory input to the plantar surface of a foot to thereby affect lower extremity kinematics and/or kinetics.

BACKGROUND

Conventional articles of footwear, including athletic footwear, have included two primary elements, namely an upper member and a sole structure. The upper member provides a covering for the foot that securely receives and positions the foot with respect to the sole structure. In addition, the upper member may have a configuration that protects the foot and provides ventilation, thereby cooling the foot and removing perspiration. The sole structure generally is secured to a lower portion of the upper member and generally is positioned between the foot and a contact surface (which may include any foot or footwear contact surface, including but not limited to: ground, grass, dirt, sand, snow, ice, tile, flooring, carpeting, synthetic grass, artificial turf, and the like). In addition to attenuating contact surface reaction forces, the sole structure may provide traction and help control foot motion, such as pronation. Accordingly, the upper member and the sole structure operate cooperatively to provide a comfortable structure that is suited for a variety of ambulatory activities, such as walking and running.

The sole structure of athletic footwear, in at least some instances, will exhibit a layered configuration that includes a comfort-enhancing insole, a resilient midsole (e.g., formed, at least in part, from a polymer foam material), and a contact surface-contacting outsole that provides both abrasion-resistance and traction. The midsole, in at least some instances, will be the primary sole structure element that attenuates contact surface reaction forces and controls foot motion. Suitable polymer foam materials for at least portions of the midsole include ethylvinylacetate ("EVA") or polyurethane ("PU") that compress resiliently under an applied load to attenuate contact surface reaction forces.

While some conventional sole structures have been useful to help control foot motion, some people have gait issues, such as excessive pronation or supination, arthritis issues, excessive inversion/eversion, and the like, that cannot be adequately addressed through conventional sole structures. Although the use of shoe inserts and orthotics has been shown to be successful in treating various ailments, their biomechanical effects on the body's lower extremities are less understood. Also, in certain instances, the use of an orthotic device underfoot becomes a crutch upon which the body may eventually come to depend. For each successive ailment, the crutch has to become more and more severe. Also, while wedge inserts for shoes have been used successfully to provide at least some relief or correction for certain gait issues, these wedges tend to become loose within the shoe resulting in discomfort and/or can be easily lost. Accordingly, there is room in the art for improvements on lower extremity motion control.

SUMMARY

Aspects of the present invention relate to new systems and methods for treating certain gait issues and overuse injuries that may be used by themselves, or in conjunction with other traditional methods, e.g., like those previously described. Furthermore, aspects of the present invention may provide long-term relief of specific movement related ailments as features of systems and methods of the invention do not, when used alone, provide a mechanical crutch.

More specific aspects of the present invention relate to controlling user motion and/or changing sensory input to the feet during ambulatory activities, such as walking or running, or during athletic or other activities that include walking, running, and/or other non-linear movements, such as cutting actions in basketball and tennis, etc., rapid stopping actions, rapid starting actions, etc., using selectively textured footbeds, such as insoles, sock-liners, interior footwear bootie members, socks, or other foot-receiving devices or portions thereof.

Some more specific aspects of this invention relate to foot-receiving devices, such as articles of footwear, that include: (a) a foot-covering member (such as an upper member); (b) a foot-supporting member (such as a sole structure) engaged with the foot-covering member; and (c) a footbed for supporting a plantar surface of a user's foot located within the foot-receiving chamber (e.g., between the foot-covering member and the foot-supporting member). In these devices, one of the lateral or medial sides of the footbed surface will have a smooth or substantially smooth surface or feel while the opposite side will have a textured surface or feel, e.g., due to the presence of plural raised areas that define the textured surface or feel. Additional aspects of this invention relate to articles of clothing, including any article of clothing that includes a chamber for receiving and/or containing a wearer's foot (such as a sock, stocking, pajamas, pantyhose, etc.). Such articles of clothing may include, for example: (a) a tubular member made at least in part from a textile material, the tubular member defining an interior chamber for receiving a foot; and (b) a footbed for engaging a plantar surface of a user's foot, wherein the footbed is engaged with or integrally formed as part of the tubular member, and wherein one of the lateral or medial sides of the footbed will have a smooth or substantially smooth surface or feel while the opposite side will have a textured surface or feel, e.g., by including plural raised areas or elements that define the textured surface or feel.

Still additional aspects of this invention relate to methods of making foot-receiving devices (such as articles of footwear) and/or articles of clothing that include footbeds of the types described above. Such methods may include providing, in some manner, a footbed of the types described above with an otherwise conventional shoe or other foot-receiving device product and/or with a conventional sock or other article of clothing product.

Further aspects of this invention relate to methods of controlling user motion, e.g., affecting a wearer's kinematics or kinetics during ambulatory activities, using products in accordance with examples of this invention. Such methods may include: (a) providing a footbed for engaging a plantar surface of a user's foot (e.g., as part of an article of clothing, as part of an article of footwear, as part of another foot-receiving device, directly on a wearer's foot, as a separate element, etc.), wherein one of a lateral side or a medial side of the footbed has a smooth or substantially smooth feel or surface, and the opposite side of the footbed has a textured feel or surface, e.g., by providing plural raised elements defining the textured surface or feel; and (b) performing an ambulatory activity while having the plantar surface of the user's foot (directly or indirectly) engaged with the footbed.

BRIEF DESCRIPTION OF THE DRAWINGS

The above and other objects, features, and advantages of the present invention will be readily apparent and fully understood from the following detailed description, taken in connection with the appended drawings, in which:

FIGS. 1A through 1C illustrate example footbed structures used in the Experimental Results section below, as well as example textured footbed structures in accordance with some aspects of this invention (FIGS. 1B and 1C);

FIG. 2 illustrates an example article of footwear in accordance with some aspects of this invention;

FIGS. 3A and 3B illustrate example articles of clothing in accordance with some aspects of this invention;

FIGS. 8A through 14B provide charts and graphs relating to various running studies performed using footbed structures in accordance with examples of this invention.

DETAILED DESCRIPTION

Figure 4:
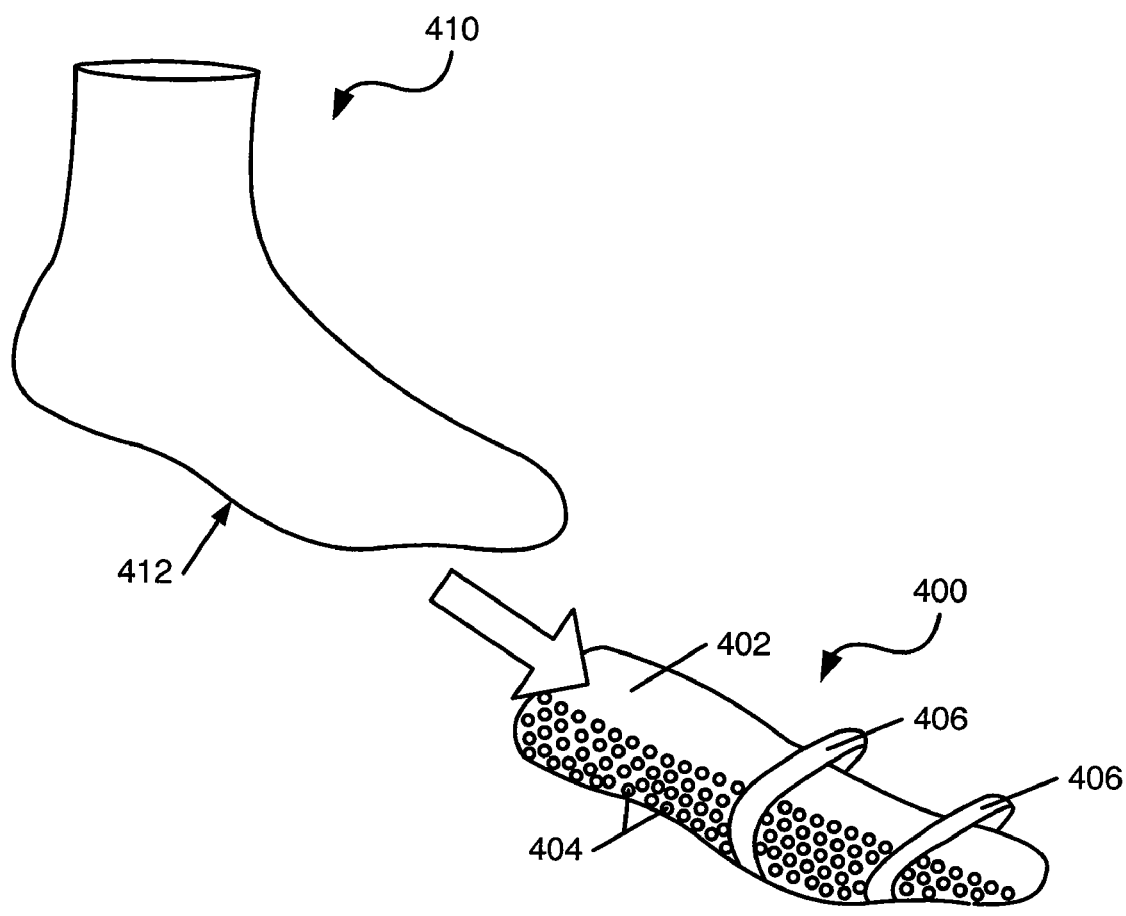
FIG. 4 illustrates an example footbed product including a footbed structure in accordance with some examples of this invention.

In the following description of various examples of the present invention, reference is made to the accompanying drawings, which form a part hereof, and in which are shown by way of illustration various structures, embodiments, and examples in which aspects of the invention may be practiced. It is to be understood that other embodiments may be utilized and structural and functional modifications may be made without departing from the scope of the present invention.

I. General Description of Aspects of the Invention

A. Products According to Examples of this Invention

Aspects of the present invention relate generally to controlling user motion and/or changing sensory input to the feet during ambulatory activities, such as walking or running, or during athletic or other activities that include walking, running, cutting actions, rapid stopping actions, rapid starting actions, etc., using selectively textured footbeds. More specific example aspects of this invention relate to foot-receiving devices, such as articles of footwear, that include: (a) a foot-covering member (such as an upper member); (b) a foot-supporting member (such as a sole structure) engaged with the foot-covering member; and (c) a footbed for supporting a plantar surface of a user's foot located within the foot-receiving chamber and/or between the foot-covering member and the foot-supporting member. In these structures, one of the lateral or medial sides of the footbed will have a smooth or substantially smooth feel or surface while the opposite side will have a textured feel or surface, e.g., by providing plural raised areas that define the textured feel or surface. In such structures, the footbed may be sized and arranged to engage all or substantially all of a plantar surface of a user's foot (e.g., the term "substantially all," as used herein in this context, means that the footbed extends to cover or engage an area corresponding to at least 80% of the plantar surface of the wearer's foot, and when specifically noted, it may extend to cover or engage an area corresponding to at least 90% or even 95% of the plantar surface of the wearer's foot). The "textured feel or surface" may be provided, sized, and/or arranged to at least predominantly cover a medial or lateral half of the footbed, and in at least some examples, to substantially cover the entire medial or lateral half of the footbed (e.g., the term "substantially cover," as used herein in this context, means that the texture feel or surface extends to cover an area corresponding to at least 80% of the medial or lateral half of the footbed, and when specifically noted, it may extend to cover an area corresponding to at least 90% or even 95% of the medial or lateral half of the footbed). The term "substantially smooth," as used herein in this context, means that the smooth feel or surface extends to cover an area corresponding to at least 80% of the medial or lateral half of the footbed, and when specifically noted, it may extend to cover an area corresponding to at least 90% or even 95% of the medial or lateral half of the footbed.

Additional aspects of this invention relate to articles of clothing, including any article of clothing that includes a chamber for receiving and/or containing a wearer's foot (such as a sock, stocking, pajamas, pantyhose, etc.). Such articles of clothing may include, for example: (a) a tubular member made at least in part from a textile material, the tubular member defining an interior chamber for receiving a foot; and (b) a footbed for engaging (directly or indirectly) a plantar surface of a user's foot, wherein the footbed is engaged with or integrally formed as part of the tubular member, and wherein one of the lateral or medial sides of the footbed will have a smooth or substantially smooth feel or surface while the opposite side will have a textured feel or surface, e.g., by providing plural raised areas that provide the textured feel or surface. The footbed may have any desired structure or arrangement, including the various structures and/or arrangements for the footbed described above and those described in more detail below.

The footbed may be provided in a variety of different ways without departing from this invention. For example, the footbed may be integrally formed as part of the foot-covering member and/or the foot-supporting member structure(s) (e.g., integrally formed as part of the upper member and/or sole structure of an article of footwear). As another example, the footbed may be provided as a separate structure engaged with one or more of the foot-covering member and/or the foot-supporting member (e.g., as part of an insole member, as part of a sock liner, as a separate insert member, etc.). As still additional examples, the footbed may be provided as an integral part of and/or attached to an article of clothing, such as a sock or other article of clothing (e.g., within the interior or on the exterior of the sock or other article of clothing, etc.). As yet another example, if desired, the footbed may constitute a separate element directly engageable with a user's foot.

B. Methods of Making Products According to Examples of this Invention

Additional aspects of this invention relate to methods of making articles of footwear (or other foot-receiving devices) including one or more of the various structures and/or features described above. Such methods may include, for example: (a) engaging an upper member (or other foot-containing member) with a sole structure (or other foot-supporting member); and (b) providing a footbed for supporting a plantar surface of a user's foot with at least one of the upper member and/or the sole structure, wherein one of a lateral side of the footbed or a medial side of the footbed has a smooth or substantially smooth feel or surface, and the opposing side of the footbed has a textured feel or surface, e.g., by providing plural raised areas defining the textured feel or surface. Any desired constructions, materials, or styles of the article of footwear (or other foot-receiving device) may be used without departing from the invention, including conventional constructions, materials, and styles that are known and used in the art. Also, the footbed may have any of the structures, arrangements, and/or constructions described above (and/or those described in more detail below).

Still additional aspects of this invention include methods of making articles of clothing that receive and/or containing a foot. Such methods may include, for example: (a) providing a tubular member made at least in part from a textile material, the tubular member defining an interior chamber for receiving a foot; and (b) providing a footbed for engaging a plantar surface of a user's foot with the tubular member, wherein the footbed is engaged with or integrally formed as part of the tubular member, and wherein one of a lateral side or a medial side of the footbed has a smooth or substantially smooth feel or surface and the opposite side of the footbed has a textured feel or surface, e.g., by providing plural raised elements defining the textured feel or surface. Any desired constructions, materials, or styles of the article of clothing may be used without departing from the invention, including conventional constructions, materials, and styles that are known and used in the art. Also, the footbed may have any of the structures, arrangements, and/or constructions described above (and/or those described in more detail below).

C. Methods of Using Products According to Examples of this Invention

Additional aspects of this invention relate to methods of controlling user motion, e.g., affecting a wearer's kinematics or kinetics during ambulatory activities, using products in accordance with examples of this invention. Such methods may include: (a) providing a footbed for engaging a plantar surface of a user's foot, wherein one of a lateral side or a medial side of the footbed has a smooth or substantially smooth feel or surface, and the opposite side of the footbed has a textured feel or surface, e.g., by providing plural raised elements defining the textured feel or surface; and (b) performing an ambulatory activity while having the plantar surface of the user's foot directly or indirectly engaged with the footbed. The footbed may be provided in a variety of ways without departing from this invention. For example, the footbed may be provided as a portion of an article of footwear, e.g., as an insole member or a sock-liner, integrally formed as part of a sole structure of the article of footwear, integrally formed as part of an upper member of the article of footwear, provided as an independent structure inserted into an article of footwear or other foot-receiving device, etc. As additional examples, if desired, the footbed may be included as a part of a sock or other article of clothing, e.g., integrally formed as part of the clothing structure (in the interior of the foot-receiving chamber or on the interior or exterior of the foot-receiving chamber), inserted into the clothing structure, attached to the exterior of the clothing structure, etc. The footbed also may constitute a separate structure that is directly attachable to a user's foot. The footbed also may have any of the various structures, constructions, arrangements, and/or characteristics described above (and/or those described in more detail below).

Various kinematic and/or kinetic characteristics of ambulatory activity may be affected using footwear or articles of clothing including footbeds of the types described above. For footbeds in which the lateral side of the footbed has a smooth or substantially smooth feel or surface and the medial side includes a textured feel or surface, examples of kinematic and/or kinetic characteristics of ambulatory activity that may be affected include the following: (a) reducing pronation while walking; (b) reducing a maximum amount of eversion while walking; (c) reducing a rearfoot range of motion while walking; (d) reducing eversion velocity while walking or running; (e) reducing plantarflexion while pushing off during a step while walking; (f) increasing maximum inversion at the end of the ground contact phase during a step while walking; (g) reducing inversion of a user's foot at heel strike while running; (h) reducing an eversion range of motion of a user's foot while running; (i) reducing an amount of inversion experienced by a user's foot at the end of a step phase while running; (j) reducing maximum internal tibial rotation while running; and (k) increasing peak active contact surface reaction force while running. For footbeds in which the medial side of the footbed has a smooth or substantially smooth feel or surface and the lateral side has a textured feel or surface, examples of kinematic and/or kinetic characteristics of ambulatory activity that may be affected include the following: (a) increasing pronation while walking; (b) increasing a maximum amount of eversion while walking; (c) increasing a rearfoot range of motion while walking; (d) increasing eversion velocity while walking or running (e) reducing peak vertical loading rate while walking; (f) increasing peak internal tibial rotation while running; (g) reducing user ankle plantar-flexor moments while running; (h) reducing user peak internal knee rotation moments while running; (i) reducing user knee peak abduction moments while running; (j) reducing peak impact while running; (k) reducing peak vertical loading while running; and (l) increasing stability during lateral cutting or direction change movements. Products in accordance with some examples of this invention also may be useful in treating arthritis (e.g., when the textured feel or surface is on the lateral side) or knee pain (e.g., when the textured feel or surface is on the medial side).

Given this general description of various features and aspects of the invention, more detailed descriptions of structures of products in accordance with this invention, as well as methods of making and using such products, follow.

II. Specific Examples of the Invention

While various aspects and features of the invention generally have been described above, the following provides more detailed, specific examples of products and methods in accordance with the invention. Those skilled in the art should understand, of course, that the following description constitutes descriptions of examples of the invention and should not be construed as limiting the invention in any way.

A. Example Products According to the Invention

FIGS. 1A through 1C generally illustrate footbeds for engaging a plantar surface of a user's foot that were used in the experimental tests described below. More specifically, FIG. 1A illustrates a smooth or untextured plantar surface contacting footbed pair 100 used as a control in the various experiments described below. FIG. 1B illustrates a plantar surface contacting footbed pair 120 in accordance with some examples of this invention that includes a "textured" surface on the medial sides 122 and a smooth or untextured surface on the lateral sides 124. FIG. 1C illustrates a plantar surface contacting footbed pair 140 in accordance with some examples of this invention that includes a "textured" surface on the lateral sides 144 and a smooth or untextured surface on the medial sides 142. The "texturing" provided in these example footbed structures 120 and 140 constitutes small raised elements 150 (e.g., hemispheres, parabolic surfaces, cylindrical structures, conical structures, cubic square structures, cubic rectangular structures, etc.) that extend upward from the base surface 152 of the footbeds 120 and 140 to contact the plantar surface of the wearer's foot.

The term "textured," as used herein, means structures of sufficient size and shape to be immediately felt by and to elicit an immediate conscious awareness to a wearer when located under the plantar surface of their foot (e.g., with weight applied via the plantar surface). The texturing may take on a wide variety of different sizes and shapes without departing from this invention. For example, as illustrated in FIGS. 1B and 1C, in this illustrated example, the texturing is provided as generally round, hemispherically raised elements 150 formed in or on the footbed base surface 152 and extending upward toward and to contact the plantar surface of a wearer's foot in use. Of course, the raised elements 150 may be of any desired shape (e.g., including those noted above), size (length, width, and/or height), distribution, and/or construction without departing from this invention. Also, if desired, the raised elements 150 and/or other texturing structures, as well as the pattern of raised elements and/or other texturing structures, may vary or change in size and/or vary in pattern or arrangement over a given footbed surface and/or between footbed surfaces of a given pair without departing from this invention.

As another example or alternative, if desired, at least some of the raised elements may extend in a direction away from the surface of the footbed that contacts the plantar surface of the wearer's foot (and optionally extend from the surface of the footbed opposite the surface that contacts the wearer's foot), provided that the overall footbed structure (e.g., insole member or sock-liner) is constructed such that the raised elements still can be felt by the wearer through the construction of the footbed.

The texturing also may be located at a variety of different positions and/or in a variety of arrangements or patterns without departing from this invention. In at least some examples, the texturing will limited to one side of the footbed construction (e.g., solely on the medial side or solely on the lateral side), or at the very least, it will be significantly more pronounced on one side as compared to the other. Where present, the texturing may be relatively evenly distributed, or it may be more concentrated in some areas as opposed to others. As some more specific examples, if desired, the "textured surface" or the "texturing" may be sized and arranged to at least predominantly cover a medial or lateral half of the footbed (optionally evenly distributed over the textured half), and in at least some examples, it will be sized and arranged to at least substantially cover the medial or lateral half of the footbed, optionally evenly distributed over the textured half of the footbed. Also footbed structures in accordance with examples of this invention may be sized and arranged to engage all or substantially all of the plantar surface of a user's foot.

The footbeds 120 and 140 may take on a wide variety of different forms, structures, and/or constructions without departing from this invention. For example, the footbeds 120 and/or 140 may be constructed as sock-liner or insole components that may be included in an article of footwear, e.g., during manufacture of the article of footwear, at a later time, etc. The raised elements 150 may be provided in such sock-liner or insole components in various ways, for example: by including additional textile material as part of the sock-liner or insole component structure at the locations of the raised elements 150; by providing plastic elements in or on the sock-liner or insole component structure (e.g., integrally forming the raised elements 150 in the sock-liner or insole structure during molding or other sock-liner or insole component forming processes, attaching the raised elements 150 (individually or in one or more groups) to a sock-liner or insole structure by adhesives, mechanical connectors, etc.); etc. As still additional examples, the footbeds 120 and 140 also may be constructed, at least in part, as air or other gas-filled bladders, optionally with the raised elements 150 integrally molded therein, attached thereto, etc. As yet additional examples, the raised elements 150 may be provided as part of a midsole or other structure underlying a conventional sock-liner or insole member, provided that the raised elements 150 are sized and shaped so as to be capable of being felt by the wearer through the sock-liner or insole member and/or provided that the raised elements extend into and/or through openings provided in the sock-liner or insole member up toward the foot's plantar surface so as to be felt by the wearer. Other footbed structures and/or arrangements also are possible.

FIG. 2 illustrates a partial view of an example article of footwear 200 that includes a footbed 120 or 140 of the types illustrated above in FIGS. 1B and 1C. The article of footwear 200 includes an upper member 202 and a sole structure 204 engaged with the upper member. The overall article of footwear 200, the upper member 202, and the sole structure 204 may be provided in any desired construction or style, from any desired number of parts and/or materials, and joined together in any desired manner, without departing from the invention, including in conventional constructions and styles, with conventional parts and/or materials, and/or joined together in conventional manners, as are known and used in the footwear art. In some examples, the article of footwear 200 may be an athletic shoe, although other types of shoes also may take advantage of constructions and features of the invention.

In the specifically illustrated example, the sole structure 204 includes an outsole member 204a and a midsole member 204b, and the upper member 202 is lasted around and engaged between the midsole member 204b and the outsole member 204a. While the midsole member 204b is illustrated as internal to the footwear structure 200 in FIG. 2, if desired, at least some portions of the midsole member 204b may be external of the shoe chamber, and outside the upper member 202. Also, in this illustrated example structure 200, the footbed 120, 140 is provided in the form of an insole or sock-liner component 120, 140, which may constitute part of the upper member structure 202 and/or the sole structure 204. Alternatively, if desired, the insole or sock-liner component 120, 140 may be provided as a separate and/or independent structure, e.g., one that is inserted into the foot-receiving chamber of an article of footwear, for example, as part of the manufacturing process, after manufacture is complete, etc. As still another example, if desired, the footbed 120, 140 may be provided as part of an interior bootie member or other structure integrally formed in and included as part of the footwear structure 200. Also, any of the various potential footbed structures and constructions described above in conjunction with FIGS. 1B and 1C may be used in the footwear structure 200 of FIG. 2 without departing from the invention.

If desired, separate means may be provided to hold the footbed 120, 140 in place with respect to the article of footwear 200. Examples of such means include, but are not limited to: mechanical connectors (such as snaps, straps, buckles, etc.); hook-and-loop type fasteners; adhesives; grooves or other retaining structures; etc.

Other footbed product structures and constructions are possible without departing from this invention. FIG. 2, as described above, illustrates example products in which the selectively textured footbed 120, 140 is included as part of a footwear structure (e.g., integrally formed as part of the footwear construction, inserted into the footwear construction, etc.). This is not a requirement. As another example, as illustrated in FIGS. 3A and 3B, products in accordance with some examples of this invention may be provided as an article of clothing 300, 320, such as socks, stockings, pantyhose, pajamas, or other garments that contain and engage the plantar surface of a wearer's foot. The article of clothing 300, 320 includes a footbed surface 302 on which plural texture elements 304 are provided. FIG. 3A illustrates an example article of clothing 300 in which the texture elements 304 are provided on the lateral side 306 of the plantar-engaging surface (and none or substantially none on the medial side 308), while FIG. 3B illustrates an example article of clothing 320 in which the texture elements 304 are provided on the medial side 308 of the plantar-engaging surface (and none or substantially none on the lateral side 306).

The texture elements 304 may be provided in an article of clothing 300, 320 in any desired manner without departing from the invention. For example, the texture elements 304 may be provided as areas of increased density of textile material integrally formed in the textile structure of the article of clothing (e.g., during the knitting, weaving, or other formation processes). As another example, the texture elements 304 may be provided as individual plastic or textile nubs that are attached to the article of clothing's 300, 320 interior and/or exterior surfaces. As still another example, if desired, the texture elements 304 may be provided as a separate component or element (akin to an insole element or sock-liner) that is inserted into the interior (i.e., the foot-receiving chamber) of the article of clothing. Also, the texture elements 304 may have any of the various sizes, shapes, structures, constructions, and/or arrangement described above, e.g., in conjunction with FIGS. 1B, 1C, and 2.

FIG. 4 illustrates another example structure 400 for providing a textured footbed in accordance with some examples of this invention. This structure 400 includes a base member 402 that defines a major surface for engaging a plantar surface 412 of a wearer's foot (e.g., directly engaging the bare foot or indirectly engaging the foot, for example, through a sock, stocking, or other article of clothing 410, etc.). The base member 402 may have any desired construction, such as a fabric or textile construction, a sock-liner type construction, an insole member type construction, an air or gas-filled bladder construction, or the like, e.g., as generally described above. One side of the base member 402 also may include texture elements 404 provided therein or thereon in any desired manner, including the various example manners described above in conjunction with FIGS. 1B, 1C, 2, and 3. Of course, the texture elements 404 may be provided in or on the base member 402 in any sizes, shapes, structures, constructions, patterns, and/or arrangement, including the various sizes, shapes, structures, constructions, patterns, and/or arrangements described above.

This example footbed structure 400 additionally includes means for (at least partially) holding the footbed structure 400 in place with respect to an article of clothing 410 and/or a wearer's foot. While any desired means for holding the footbed structure 400 in place may be provided without departing from the invention, in this illustrated example structure 400, one or more elastic bands 406 are provided to wrap around the wearer's foot (e.g., across the plantar surface and/or the instep portion of the foot) to at least partially secure the footbed structure 400 to the wearer's foot (optionally through a sock or other article of clothing 410). Of course, elastic bands 406 of the types illustrated in FIG. 4 may be provided in any desired sizes, in any desired shapes, and/or at any desired locations without departing from the invention. Additionally or alternatively, if desired, an elastic band or strap or other engaging system may be provided at the heel area (e.g., to extend around the wearer's heel) to help keep the footbed structure 400 in place with respect to the heel. Also, insertion of the footbed structure 400 into an article of footwear (not shown) may be relied upon, if desired, to help hold the footbed structure 400 in place with respect to the wearer's foot. As still another alternative, if desired, the footbed structure 400 could be inserted into the interior chamber of the article of clothing 410 without departing from this invention (in that event, separate engaging means, such as elastic straps 406, may be unnecessary, although some engaging means still may be provided, if desired, to help keep the footbed structure 400 in place with respect to the wearer's foot).

A wide variety of structures or systems may be used as means for holding the footbed structure 400 in place (e.g., with respect to a foot, article of clothing, or article of footwear) without departing from this invention. For example, the footbed structure 400 may be held in place by hook-and-loop fasteners, snaps, straps, buckles, retaining grooves, other retaining structures, or other mechanical connector or fastener arrangements. As additional examples, the footbed structure 400 may be held in place by wrapping another element around both the footbed structure 400 and the article to which it is to be attached. This wrapping element may be an elastic bandage, tape or other adhesive, an additional sock member or article of clothing, etc. Adhesives also may be used to secure the footbed 400 to another article. Any desired manner of securing the footbed structure 400 with an article of clothing 410 or any other structure or member, including directly to a user's foot, may be used without departing from this invention.

While the specific example illustrated in FIG. 4 illustrates the footbed structure 400 engaged with an article of clothing 410, those skilled in the art will appreciate that it may be engaged with an article of footwear without departing from this invention. If desired, a means for securing the footbed structure 400 in place with respect to the article of footwear may be provided without departing from this invention. As more specific examples, hook-and-loop fasteners, snaps, straps, buckles, retaining grooves, other retaining structures, or other mechanical connector or fastener arrangements may be used; wrapping elements, such as an elastic bandage, tape or other adhesive, an additional sock member or article of clothing may be used; adhesives or cements may be used; etc.

Footbeds in accordance with some examples of this invention (e.g., as separate elements, integrally formed with an article of footwear, integrally formed with an article of clothing, etc.) may be used in any desired manner without departing from the invention. Once provided in direct or indirect contact with the plantar surface of a wearer's foot in any desired manner (e.g., by donning a sock or other article of clothing including the footbed, by donning an article of footwear or other foot-receiving device including the footbed, etc.), the wearer may walk, run, or otherwise conduct ambulatory activity with the textured surface of the footbed in contact (directly or indirectly) with the plantar surface of the foot. Stimulation of the wearer's foot via the textured surface induces motion control and/or changes the motion, kinematics, and/or kinetics associated with lower extremities in various ways, as will be described in more detail below.

The various example structures described above typically included footbed component pairs in which the left footbed component was a mirror image of the right footbed component. Of course, this is not a requirement. If desired, the footbed components of a pair may differ in texture element structures, arrangements, patterns, locations, numbers, etc. without departing from the invention, e.g., depending on specific uses, gait issues being addressed, etc. In fact, if desired, one footbed component of a pair need not include any texturing.

B. Experimental Results

Various kinematic and kinetic experiments were conducted on the effects of changing sensory input to the plantar surface of a user's foot using textured footbed structures, e.g., of the types illustrated in FIGS. 1B and 1C.

1. Examining the Effects of Changing Sensory Input to Feet While Walking

This experiment examined changes in walking kinematics of various test subjects as a result of the presence of selectively textured footbeds of the types illustrated in FIGS. 1B and 1C. In this experiment, 12 subjects (8 males and 4 females—mean height=5'9", mean weight=161 lb., shoe size 9M) were tested while walking along a 50 meter indoor pathway at a cadence of approximately 108 steps/minute. The subjects wore, at different times, a smooth (non-textured) sock-liner of the type illustrated in FIG. 1A as a control, as well as a pair of medially textured sock-liners of the type illustrated in FIG. 1B and a pair of laterally textured sock-liners of the type illustrated in FIG. 1C (the interventions were applied bilaterally, in a random order). In this experiment, the insoles or sock-liners were worn barefoot (i.e., without shoes—the subjects wore nylon stockings), and an athletic wrap held the insole or sock liner to the subjects' feet. The term "textured," as used herein, means that the textures at the plantar contact surface were strong enough to elicit an immediate conscious awareness to the wearing subject but not reported to be painful.

A motion analysis system (240 Hz) and a Kistler force plate (1000 Hz) were used to monitor and capture data in these walking tests. Specifically, ankle joint kinematics (inversion, eversion, plantarflexion, dorsiflexion, tibial rotation, etc.) and vertical ground reaction forces were evaluated.

Figure 5B:
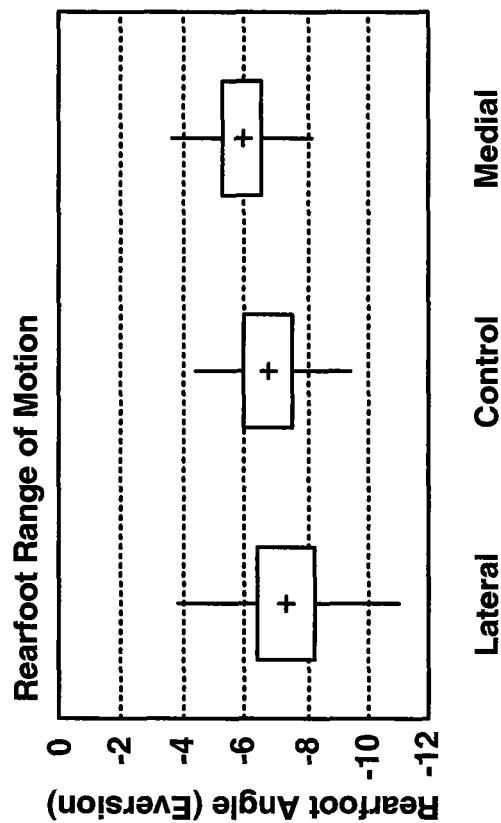
FIGS. 5A through 7 provide charts and graphs relating to various walking studies performed using footbed structures in accordance with examples of this invention.
Figure 5A:
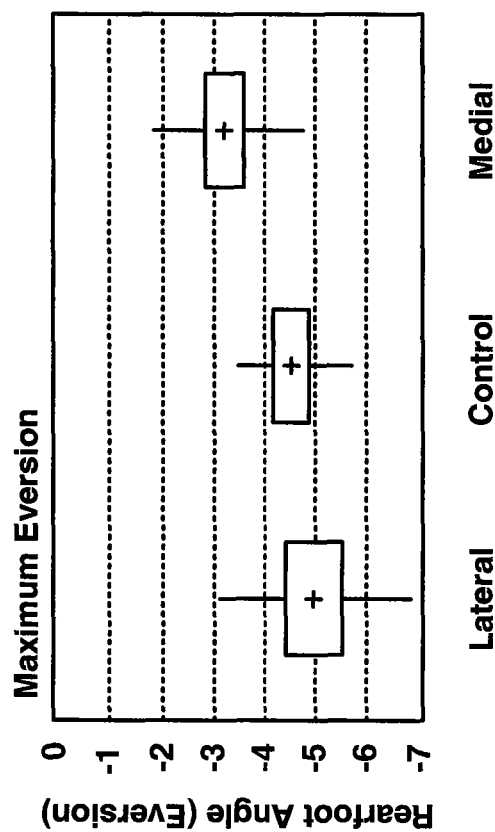
Figures 6A, 6B:
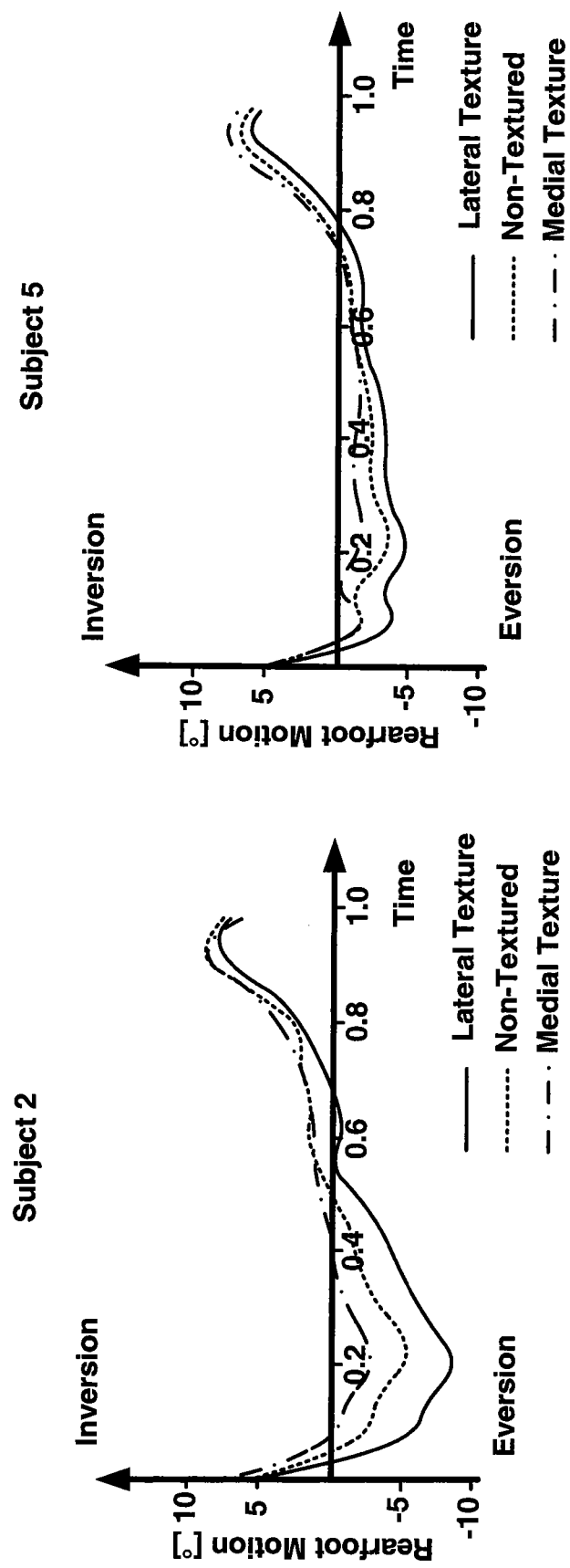

In these tests, some significant differences in rearfoot motion were observed in users while wearing the different footbed elements. For example, as illustrated in FIGS. 5A, 6A, and 6B, the maximum eversion level experienced by wearers was significantly lower with the medially textured insole components as compared to the control (non-textured) and laterally textured insole components. More specifically, FIG. 5A provides "box plots" of Maximum Eversion Levels (based on Rearfoot Angle Measurements) during the ground contact phase while walking for the collection of subjects wearing the various insole structures (in these and other similar figures, unless otherwise noted, mean values are shown as a plus sign, with standard errors defining the height of the box, and the standard deviation range defined by the solid lines extending from the boxes). FIG. 5B provides box plots of Rearfoot Range of Motion measurements (rearfoot movement from touchdown to the point of maximum eversion) during the ground contact phase while walking for the collection of subjects wearing the various insole structures. FIGS. 6A and 6B illustrate mean "Rearfoot Motion" graphs for two of the subjects while wearing each of the three insole structures. The graphs of FIGS. 6A and 6B (as well as other similar graphs included in the figures, unless otherwise noted) have been normalized in time from touchdown (at time t=0) to takeoff (at time t=1.0) during the ground contact phase.

As evident from these charts and graphs, the maximum eversion (the overall minimum point in FIGS. 6A and 6B) was smaller for the medially textured insole samples as compared with the "non-textured" control samples, but the maximum eversion generally was smaller for the control samples than it was for the laterally textured insole samples (although this latter difference was not found to be statistically significant and may be due to the limited range of eversion motion at the ankle joint when walking). Overall rearfoot range of motion (rearfoot movement from touchdown to the point of maximum eversion) was significantly lower for the medially textured insole components as compared to the other two conditions. While the laterally textured insole components generally resulted in a higher range of motion than the non-textured control condition, this difference was not found to be statistically significant. No significant differences in inversion angles at touchdown were observed between the three test conditions (note FIGS. 6A and 6B at time t=0)

The collected data also indicated that the maximum amount of inversion that occurs late in the ground contact phase (toward time t=1) was significantly higher for the medially textured insole structures as compared to the laterally textured insole structures. Eversion velocity was found to be significantly faster for the laterally textured insole structures when compared to both the medially textured insole structures and the non-textured insole structures. No significant differences in maximum inversion velocity toward the end of the stance phase were observed in these test subjects.

Figure 7:
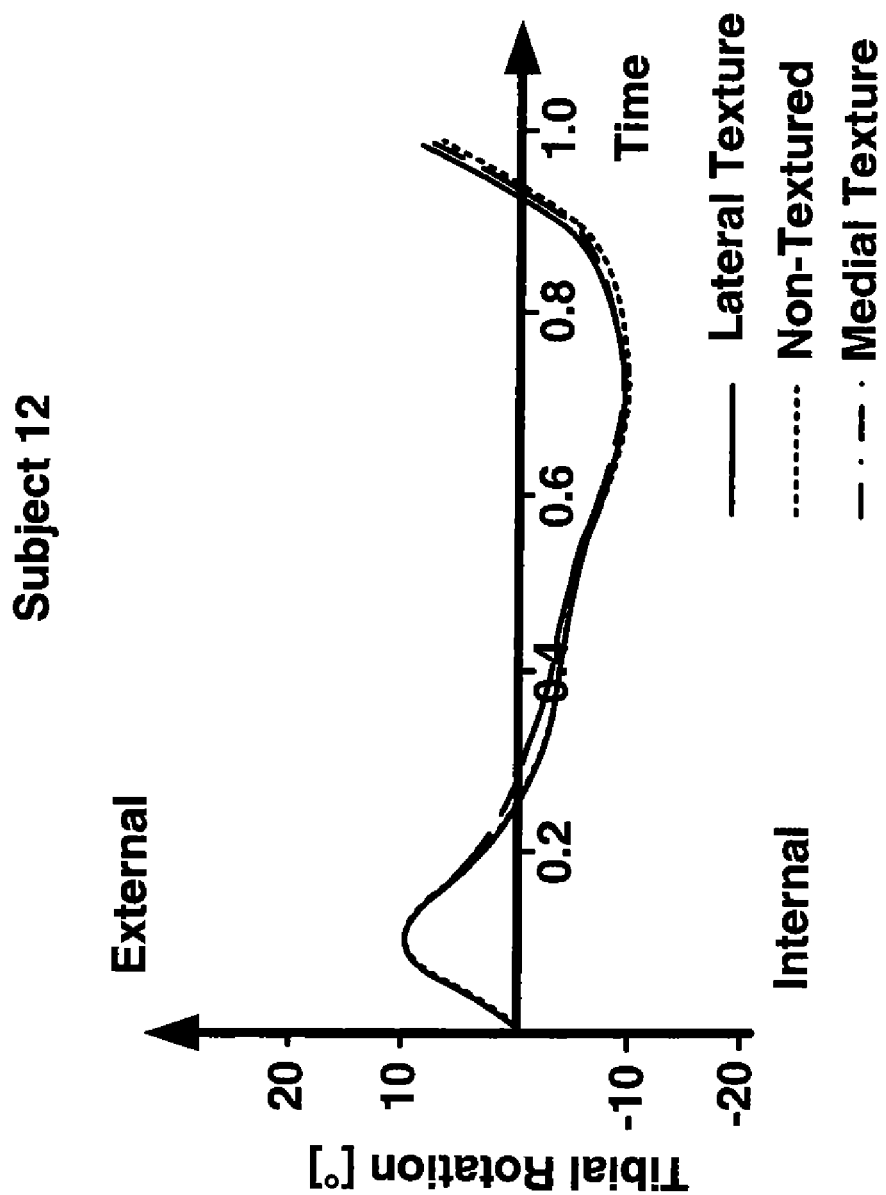

Studies also were conducted regarding the effects of use of the various selectively textured footbed structures on tibial motion while walking. The motion of the tibia is coupled with motion of the subtalar joint, and it generally would be expected that differences in rearfoot motion were reflected by differences in rotation of the tibia during the ground contact phase. However, as illustrated in FIG. 7 (which shows mean tibial rotation curves for a representative subject during ground contact using the three different footbed components), no significant differences were found in: (a) tibial rotation at foot strike (time t=0), maximum internal rotation (the peak below the graph's abscissa), or maximum external rotation of the tibia (the peak above the graph's abscissa). This is not to suggest, however, that for some subjects, tibial rotation will not be affected by the use of textured shoe inserts, socks, sock-liners, or other textured footbed products in accordance with examples of this invention.

Other kinematic differences were observed depending on the structure of the insole components worn. For example, when the wearer's foot left the ground at the end of ground contact, subjects tended to have less plantarflexion while wearing the medially textured insole components as compared to when they were wearing the laterally textured insole components. This result may suggest that subjects were not pushing off the same way when wearing the different footbed components. No significant differences in sagittal plane ankle angles (e.g., plantarflexion, dorsiflexion, etc.) at touchdown were observed in the subjects during this walking study.

Further differences were observed in the ground reaction forces experienced by wearers depending on the type of selectively textured footbed structure they were wearing. For example, the peak vertical loading rate experienced by wearers was observed to be significantly lower using the laterally textured insole components as compared to the control components (no significant differences in vertical loading rates were observed between use of the medially textured components and the control components). Recalling that the lateral heel generally is a wearer's first point of contact with the ground during a walking step, these results suggest that when a texture is placed under the lateral heel, some form of compensation occurs to alter the wearer's lower extremity motion and to reduce the loading rates during initial ground contact. It may be that increased eversion velocities observed during this time frame with the laterally textured footbed components helped to reduce the vertical loading rates.

These experimental results demonstrated that rearfoot motion can be influenced by altering sensory input to the plantar surface of the foot while walking. Additionally, as demonstrated by these tests, rearfoot motion can be modified without conventional mechanical interventions, such as wedges, dual density foams, or other prophylactics.

In general, the addition of texture to specific regions under the foot caused the foot to move away from the areas of increased sensory input. While wearing medially textured footbed components, subjects had significant reductions in rearfoot eversion (pronation). This may have been due to a conscious or subconscious attempt to keep the food from loading the medial portion of the shoe insert. Although not significant, a similar trend was seen as subjects tended to evert more when the lateral side of the shoe insert was textured.

Further support for this theory comes from the fact that subjects generally were more inverted (supinated) at the end of the stance phase while wearing the medially textured footbed components. Also, eversion velocity was significantly faster for subjects while wearing the laterally textured footbed components. As the lateral part of the foot generally is the first point of ground contact, this result may have been an attempt at moving away from the texture to load the medial side of the foot.

Influencing human motion with sensory inputs with the plantar surface of the foot, e.g., in the manners described above, may have applications in a number of products. For example, shoes (or insoles for shoes or other products, e.g., like those described above) could be provided that supplement current motion control technologies using textures to help limit excessive pronation. As another example, a manufacturer, health care provider, wearer, or other may consider the effects of adding textures to the lateral edge of basketball or other athletic footwear (e.g., by including laterally textured insoles or sock-liners) to improve stability, e.g., in cutting movements, when rapidly changing directions, starting, or stopping, etc.

2. Examining the Effects of Changing Sensory Input to Feet While Running

This experiment examined changes in running kinematics and kinetics of various test subjects as a result of the presence of selectively textured footbeds of the types illustrated in FIGS. 1B and 1C. In this experiment, 11 subjects (7 males and 4 females—mean height=5'9", mean weight=161 lb., shoe size 9M) were tested while running along a 50 meter indoor pathway at a speed of 7.5 minutes per mile (±5%). The subjects wore, at different times, Air Pegasus running shoes (commercially available from NIKE, Inc. of Beaverton, Oreg., U.S.A) with insoles of the various types illustrated in FIGS. 1A through 1C (the interventions were applied bilaterally, in a random order). Again, the term "textured," as used herein, means that the textures at the plantar contact surface were strong enough to elicit an immediate conscious awareness to the wearing subject but not reported to be painful.

A motion analysis system (240 Hz) and a Kistler force plate (1000 Hz) were used to monitor and capture data in these running tests. Specifically, ankle and knee joint kinematics and kinetics and vertical ground reaction forces were evaluated.

Figure 9B:
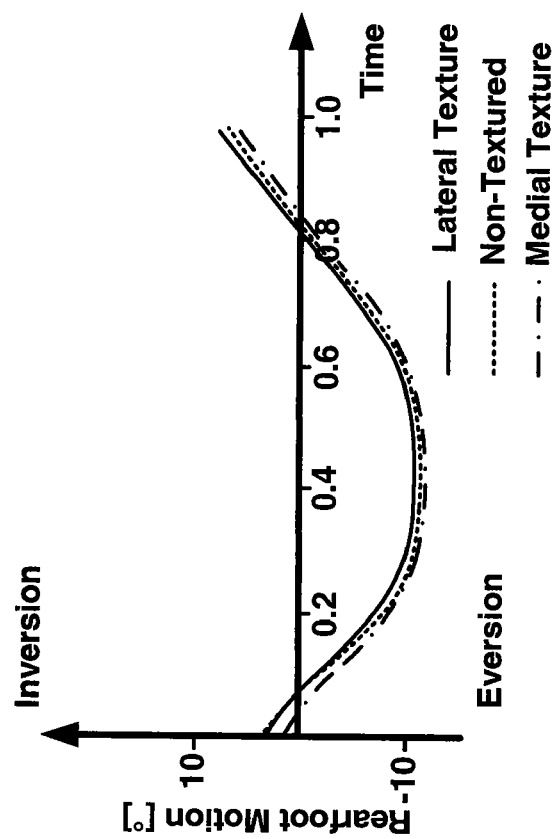
Figure 9A:
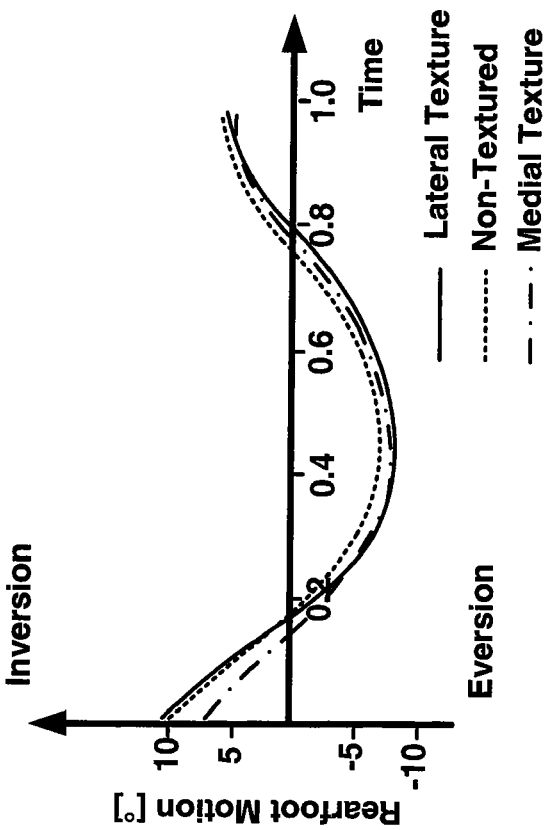

Various differences in rearfoot motion were observed under the various different test conditions. FIG. 8A contains box plots (mean, standard error, and standard deviation, as described above) showing mean rearfoot inversion angles at touchdown for the collection of test subjects under the three sets of test conditions, and FIG. 8B contains box plots showing mean eversion range of motion data for the collection of subjects under the three sets of test conditions. FIGS. 9A and 9B illustrate mean rearfoot inversion/eversion graphs for two representative subjects running using the three footbed insert conditions.

As observable from the data contained in FIGS. 8A, 9A, and 9B, subjects tended to be less inverted at heel strike while wearing the medially textured footbed components as compared to the other two shoe conditions. No significant differences in inversion angle at heel strike were observed between the laterally textured and smooth footbed conditions. Also, no significant differences were found in maximum eversion angle during the ground contact phase when using the various footbed components.

The eversion range of motion (rearfoot motion from touchdown (t=0) to the point of maximum eversion) was significantly less for the medially textured footbed components as compared to the other two conditions. This difference may be due, at least in part, to the aforementioned differences in inversion at heel strike. At the end of the stance phase (toward time t=1), subjects tended to be significantly less inverted when using the medially textured insole member as compared to the other two conditions.

Figure 10:
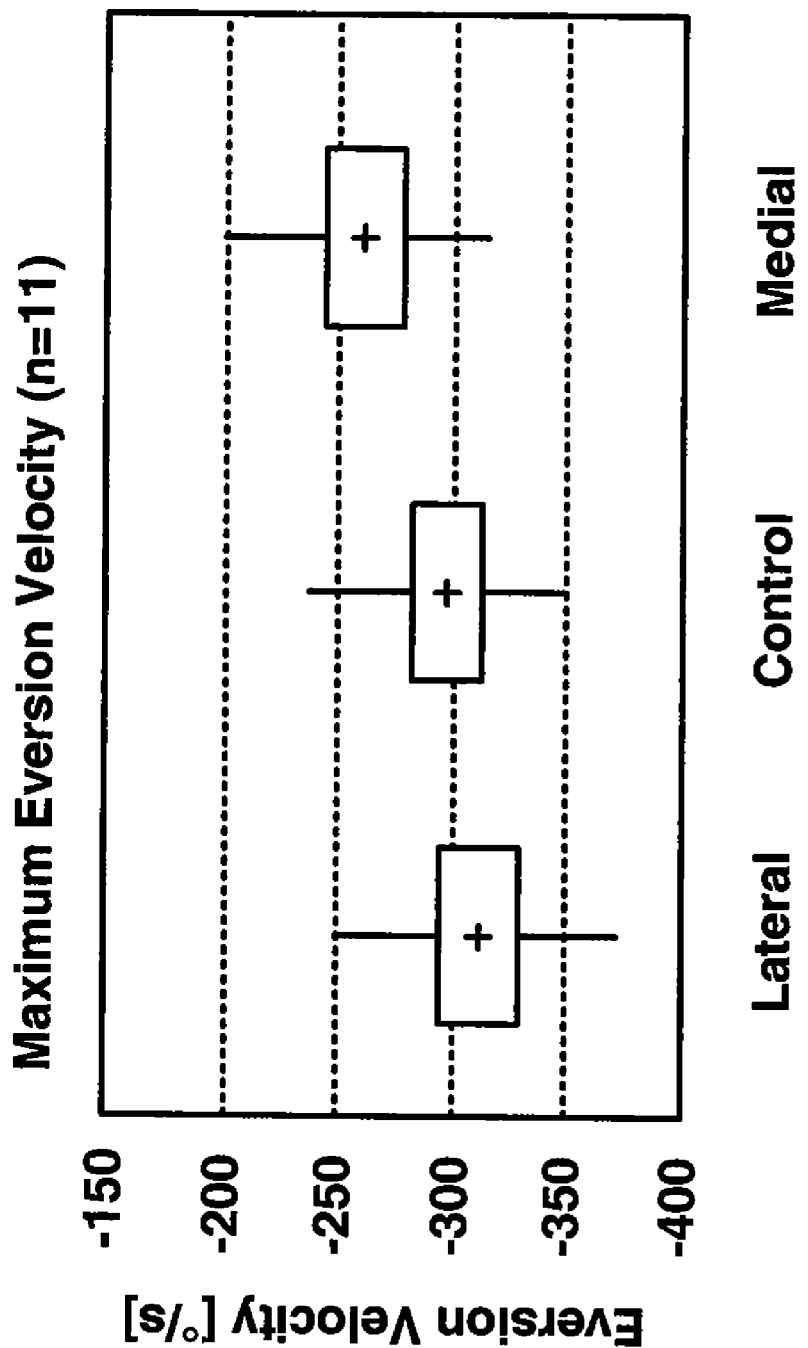

Eversion velocity data also was evaluated during these tests. Maximum eversion velocity tended to be significantly slower during use of the medially textured footbed components as compared to both the laterally textured and non-textured conditions. The maximum eversion velocity collected during this test is summarized in FIG. 10, which illustrates box plots showing the mean eversion velocity while running with the three shoe insert conditions. Additionally, these test revealed that using the laterally textured footbed components resulted in significantly faster peak eversion velocities than the non-textured conditions.

Figure 11B:
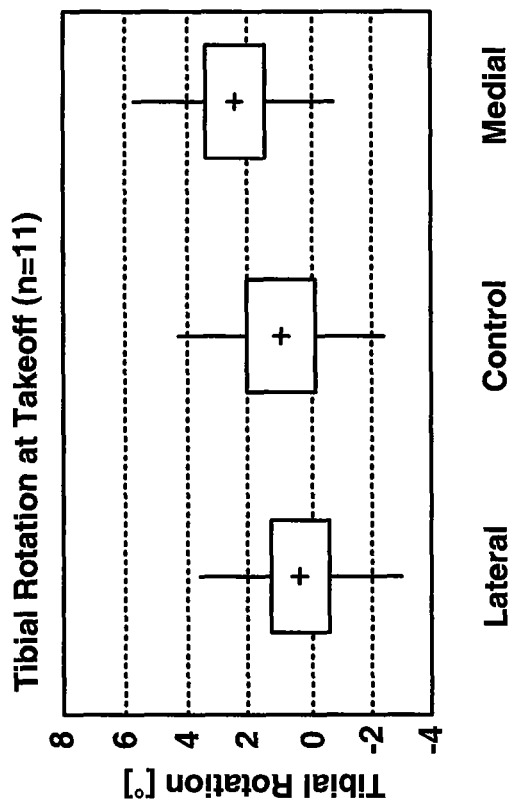
Figure 11A:
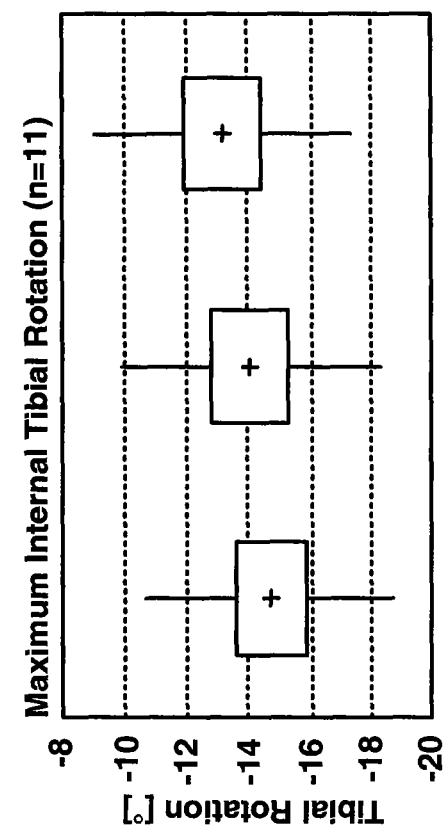
Figure 12B:
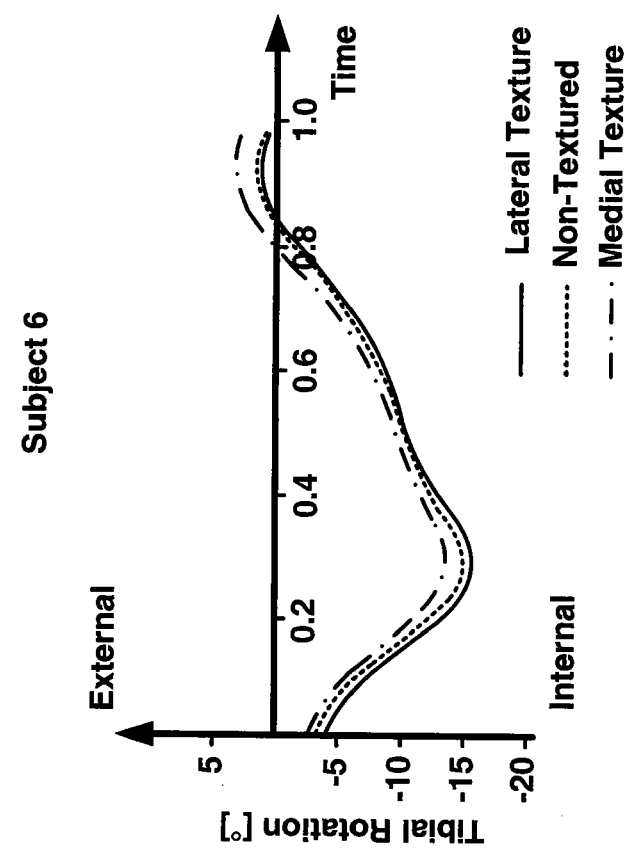
Figure 12A:
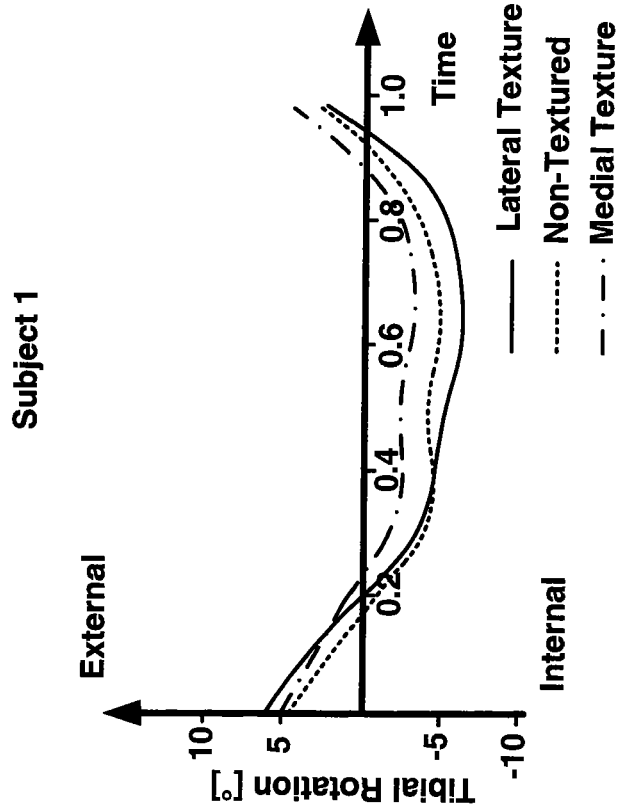

Tibial rotation data also was observed and collected during these experiments, and some of this collected data is summarized and/or illustrated in FIGS. 11A, 11B, 12A, and 12B. FIGS. 11A and 11B provide box plots illustrating mean peak internal tibial rotation (FIG. 11A) and external tibial rotation at takeoff (FIG. 11B) for the collected subjects under the various test conditions. FIGS. 12A and 12B illustrate mean tibial rotation graphs with respect to time (normalized, as described above) for two representative subjects while running in the three insert conditions.

From these tests, no significant differences in tibial rotation at heel strike were noted between the three different footbed conditions. Maximum internal tibial rotation was significantly lower for the medially textured footbed condition as compared to the control condition. Conversely, peak internal tibial rotation was significantly greater for the laterally textured footbed condition as compared to the control and the medially textured conditions. Note FIGS. 11A, 12A, and 12B. At takeoff, significantly greater external tibial rotation was observed while wearing the medially textured footbed components as compared to both of the other footbed conditions. Note FIGS. 11B, 12A, and 12B.

Figure 13A:
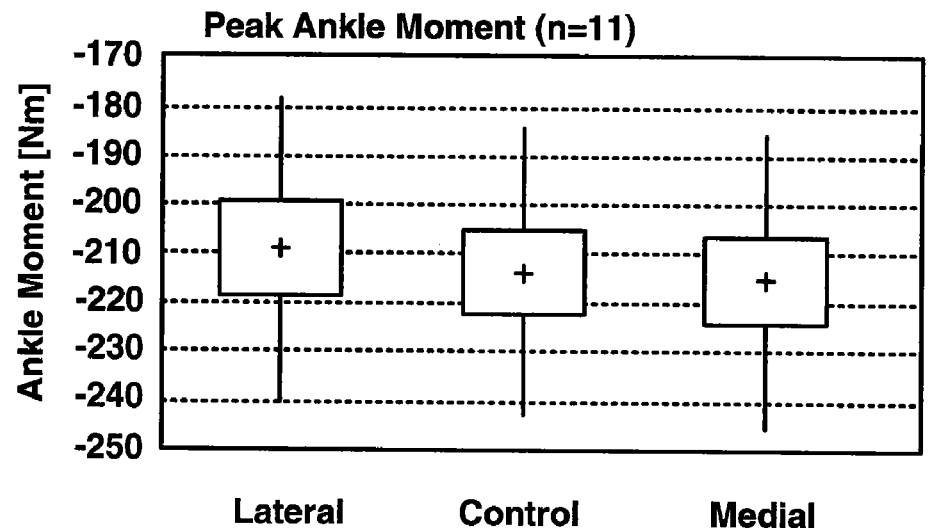
Figure 13B:
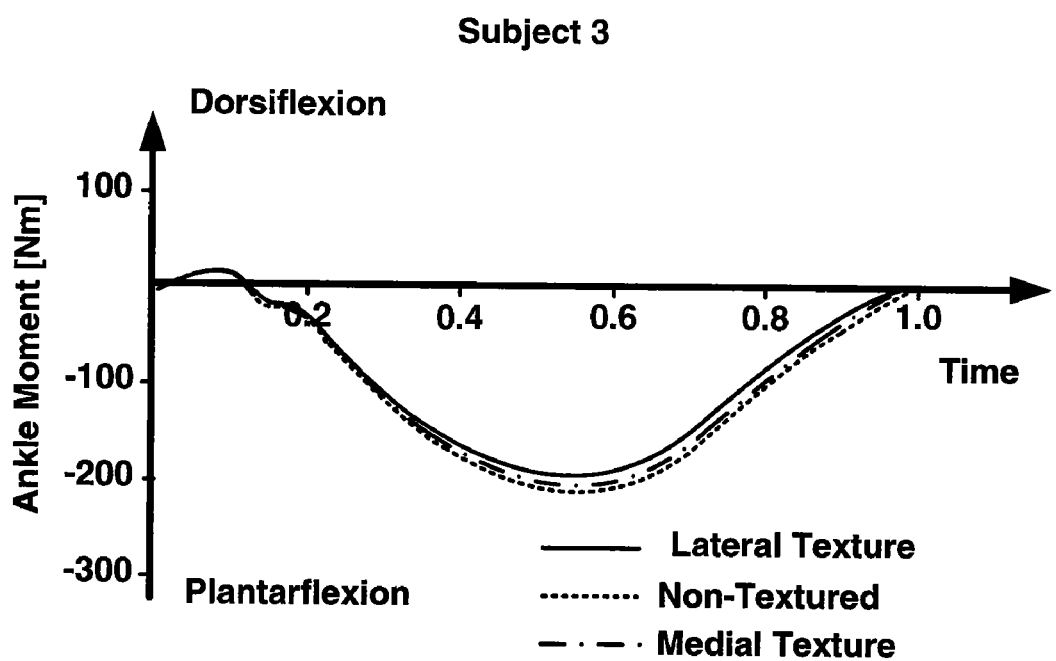

The effects of the different test footbed conditions on the ankle joint also were evaluated during these experiments. FIGS. 13A and 13B illustrate and summarize a portion of the collected data. More specifically, FIG. 13A provides box plots showing mean peak ankle plantar-flexor moments while running using the three footbed test conditions. FIG. 13B illustrates mean sagittal plane ankle moments observed for one representative subject running under the three different test conditions. No significant differences in peak abduction or adduction moments or inversion or eversion moments at the ankle joint were observed while running using the different footbed conditions. However, a small but significant reduction in peak plantar-flexor moments at the ankle joint was observed for users wearing the laterally textured footbed inserts as compared to the other two inserts.

Figure 14A:
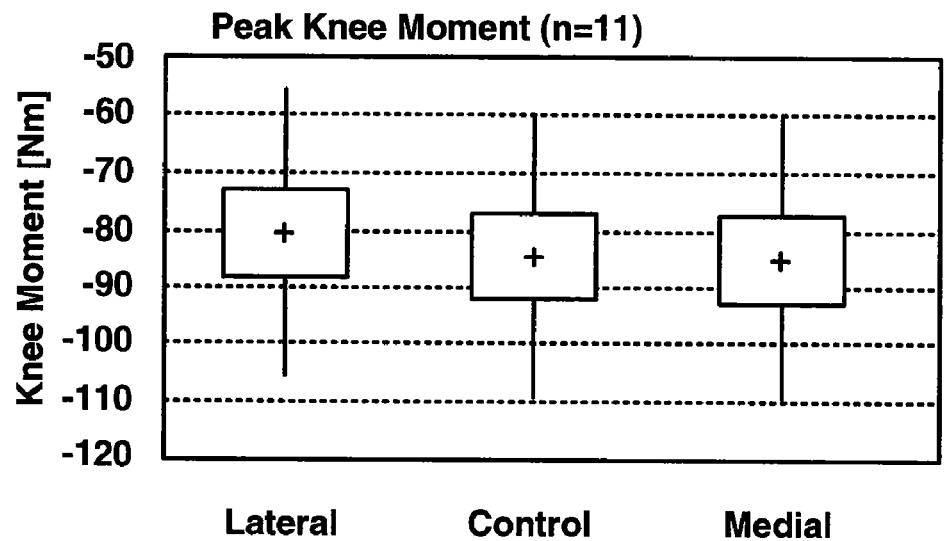
Figure 14B:
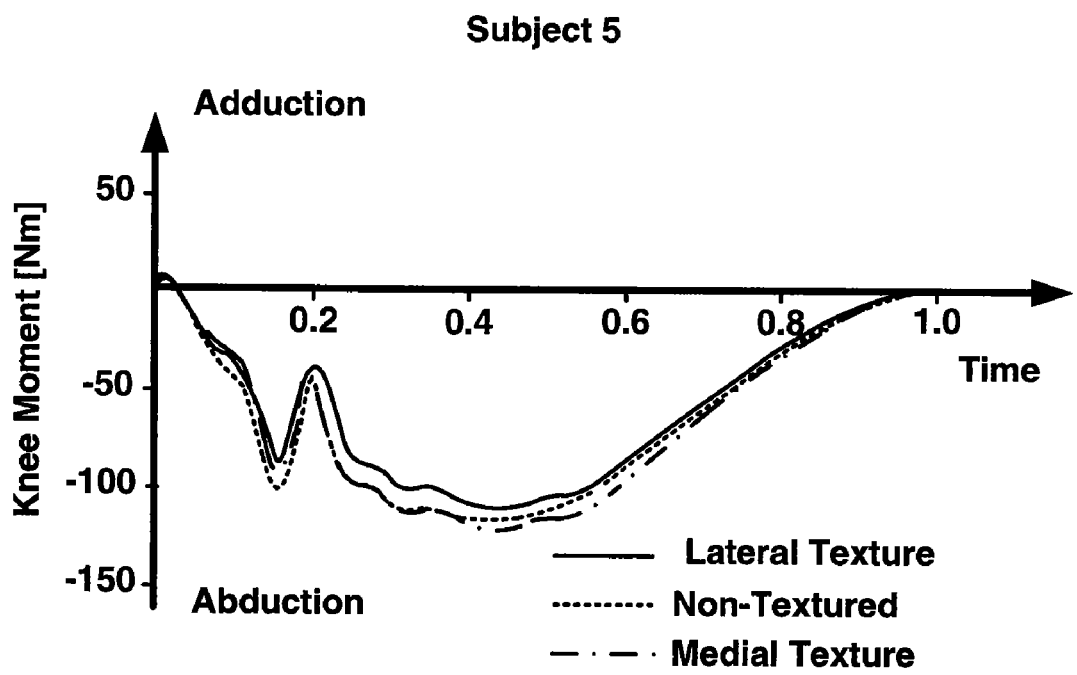

The effects of the different test footbed conditions on the knee joint also were evaluated. FIGS. 14A and 14B illustrate and summarize a portion of the collected data. More specifically, FIG. 14A provides box plots showing the mean peak knee abduction moments while running using the three footbed test conditions. FIG. 14B illustrates mean knee abduction moments observed for one representative subject running under the three test conditions. This testing showed that peak internal rotation moments were significantly lower when using the laterally textured footbed members as compared to the medially textured footbed members. Also, peak abduction moments at the knee were found to be significantly lower when using the laterally textured footbed members as compared with the other two footbed conditions. No significant differences were observed in the peak flexion moments at the knee.

The effects of the use of the various footbed conditions on vertical ground reaction forces while running also were evaluated during these tests. No significant differences in vertical impact peak were observed while running under the different footbed test conditions. However, a general reduction in impact peak was observed with the laterally textured footbed components as compared to the medially textured footbed components ($p=0.11$). Peak vertical loading rates were found to be significantly lower while running using the laterally textured footbed components as compared to the medially textured footbed components. A similar trend was seen when comparing the laterally textured condition to the control (smooth) condition ($p=0.12$). These findings may be related, at least in part, to the increased eversion velocities found while wearing the laterally textured footbeds. Also, a small, but significant increase in peak active ground reaction forces was observed when running with the medially textured footbed components as compared to the other two conditions.

Various observations can be made and/or conclusions can be drawn from the above test results. For example, as noted from the walking tests described above, stimulating the medial side of the plantar foot with textured materials tended to reduced eversion (or pronation) of the foot. In the running study, however, maximum eversion was not found to be affected during running with the textured insoles (although differences in rearfoot motion were observed during the running test, particularly at the beginning and end of stance or ground contact phase).

The slower eversion velocities observed during the running tests with the medially textured footbeds and the faster eversion velocities observed with the laterally textured footbeds support the hypothesis that the foot will attempt to limit the degree of loading on the textured surfaces. This finding, however, together with the results from the vertical ground reaction forces, is different than results typically found during running studies (typically, faster eversion velocities are associated with higher vertical loading rates). In this present running study, controlling eversion may have been associated with a motor pattern aimed at limiting loading the lateral textured areas of the foot. In other running studies, higher eversion rates may be considered a mechanical effect caused by the material properties of the midsole in the lateral heel of some running shoes.

Many observers believe that knee pain in runners, in at least some instances, may be a result of excessive internal rotation of the tibia during the ground contact phase of running. Because of strong coupling at the subtalar joint, the most common method of controlling tibial rotation is to limit eversion of the foot. Although definite reductions in eversion were not found during these tests, the present running tests indicated that the medially textured footbed did help limit internal rotation of the tibia. Conversely, these test results indicated that the laterally textured footbed conditions increased maximum internal rotation of the tibia. This knowledge provides a design for running shoes, intended to alleviate knee pain, e.g., by providing a footbed, sock-liner, or insole in the shoes including medial texturing (or otherwise providing a medially textured footbed component).

It has been known for some time that lateral wedges under the foot can be used to reduce abductor moments at the knee and alleviate chronic knee pain associated with osteoarthritis. The present testing, however, demonstrates that these same motion control results can be achieved without a mechanical intervention underfoot. These facts lead to a footwear design for arthritic patients or others that includes laterally textured footbeds, sock-liners, insole members or other laterally textured structures.

These tests demonstrate that selectively textured footbeds for articles of footwear, clothing, and/or other foot-receiving devices also may be used to supplement current motion control technologies, such as dual density foams, foot bridges, midsole constructions, etc. Textured footbeds also may be added to specific and selective anatomical regions under foot in an attempt to improve dynamic stability in sports, such as in tennis or basketball shoes (e.g., by providing laterally textured insole members for use in shoes for activities where rapid direction changes, cuts, quick lateral starts and stops, etc. are made).

While the results of these studies and the above remarks are based on the collected data, as described above, those skilled in the art will understand and appreciate that this data may not be 100% representative of everyone in a population. There may be "subject specific" responses to the textured elements that may indicate the need for tailoring the specific "feel" and/or location of the texturing when applied to a foot to obtain the desired results. Such tailoring may be accomplished through routine experimentation.

C. Additional Example Products According to the Invention

A wide variety of arrangements of texturing may be provided in footbed products without departing from the invention (e.g., footbed products may be included as part of articles of footwear, such as insole members, sock-liners, interior bootie members, etc., and/or as part of other foot-receiving devices and/or articles of clothing that contain the foot (e.g., socks, stockings, pajamas, pantyhose, etc.).

Figure 15B:
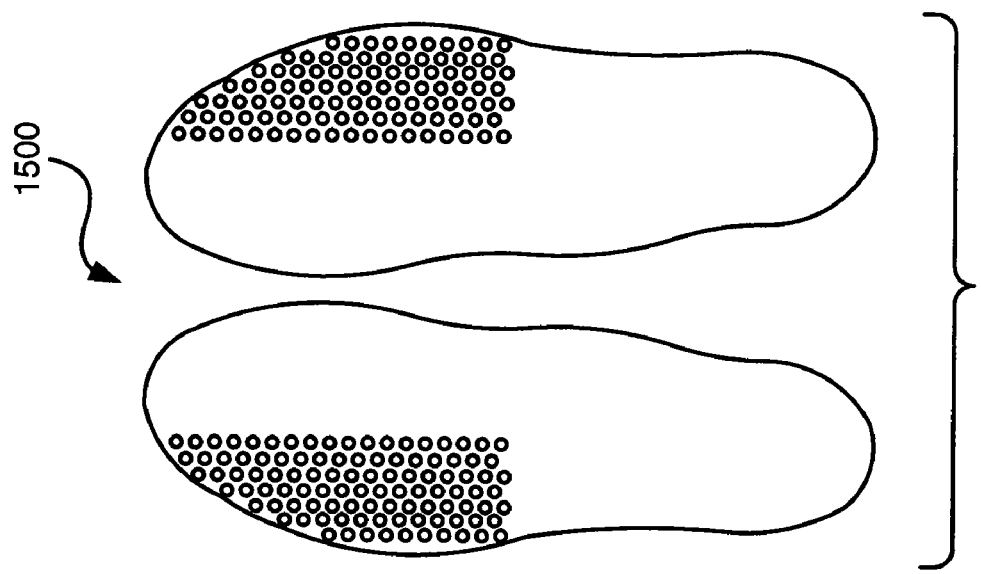
FIGS. 15A through 15N illustrate additional example arrangements of texturing elements on footbeds of foot-receiving device products according to this invention.
Figure 15A:
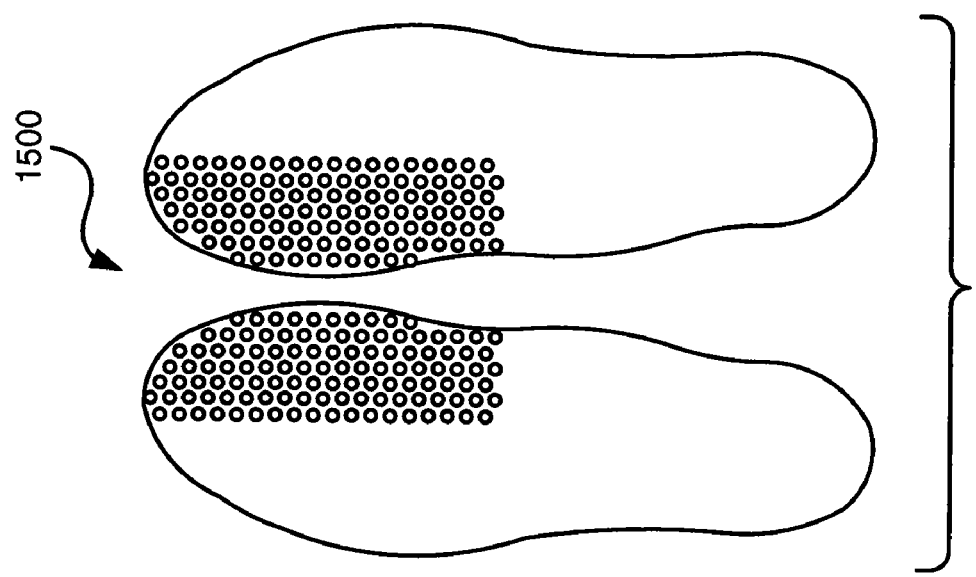
Figure 15C:
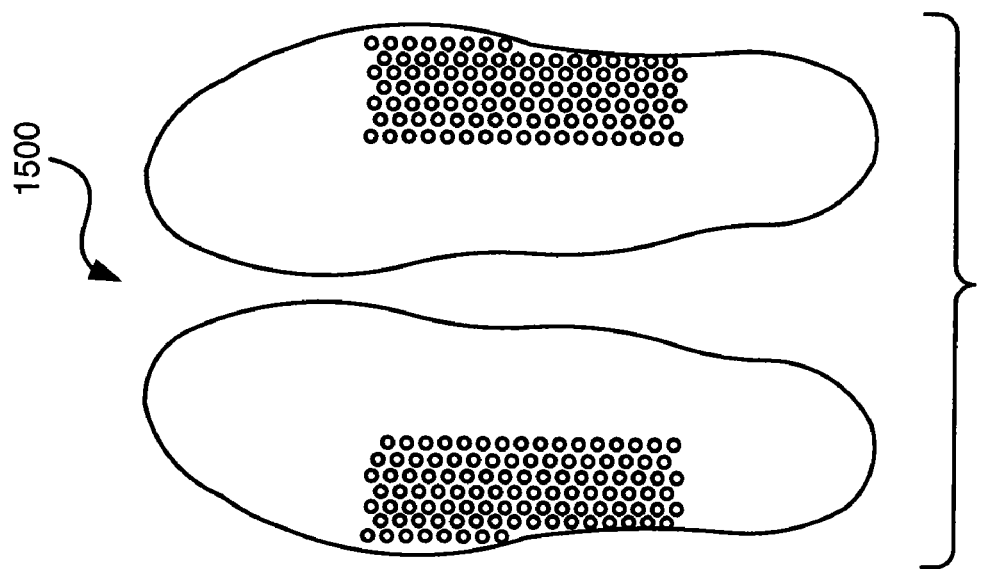
Figure 15D:
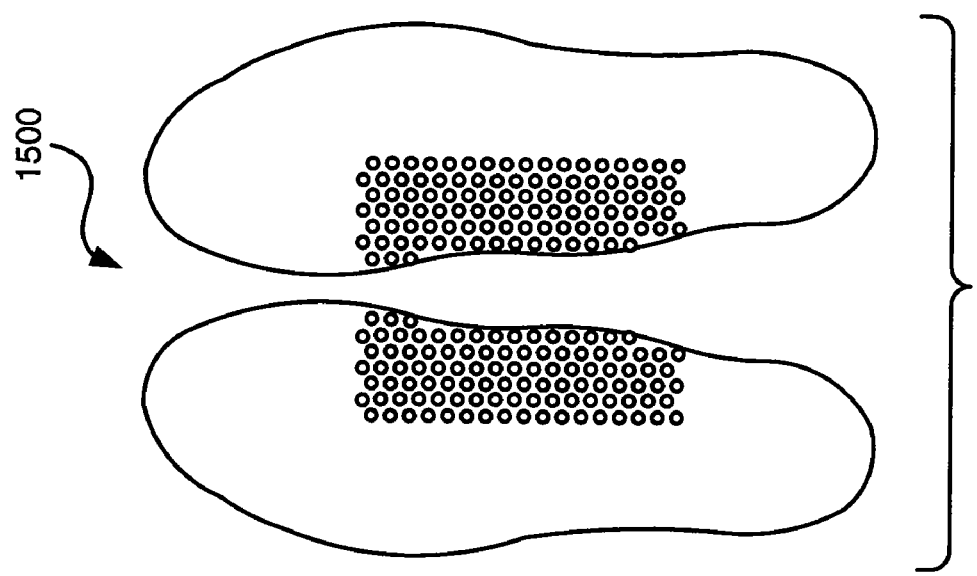
Figure 15E:
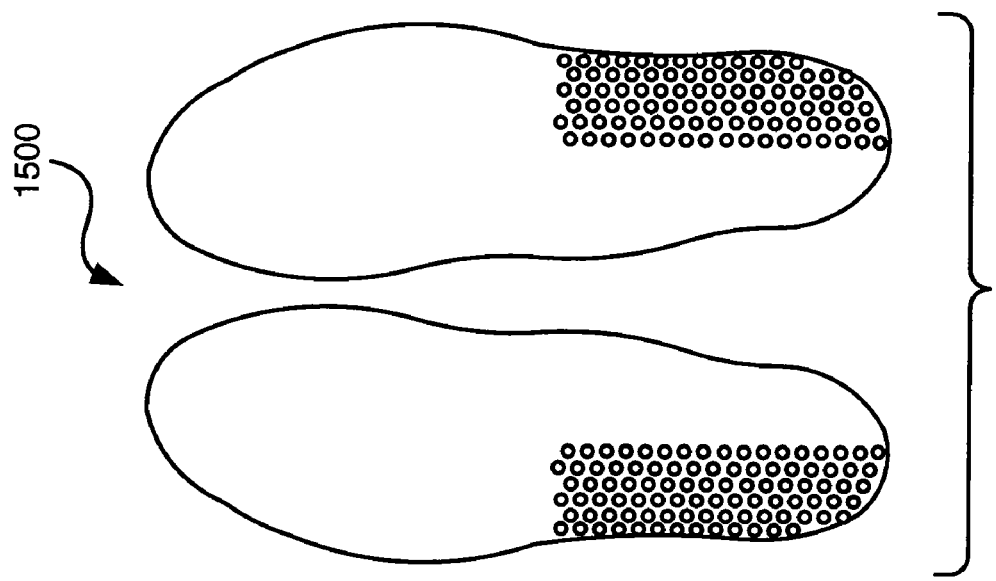
Figure 15F:
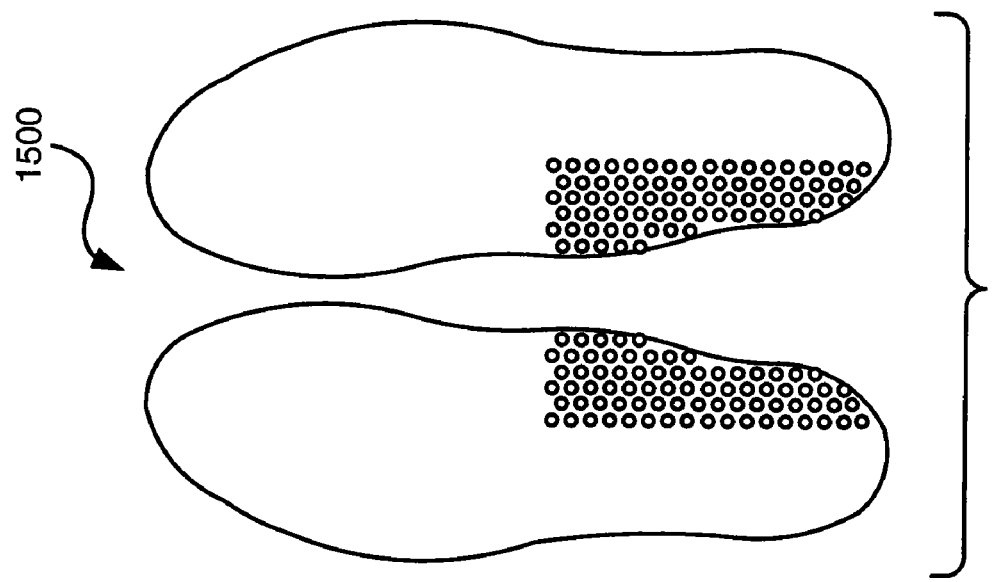
Figure 15H:
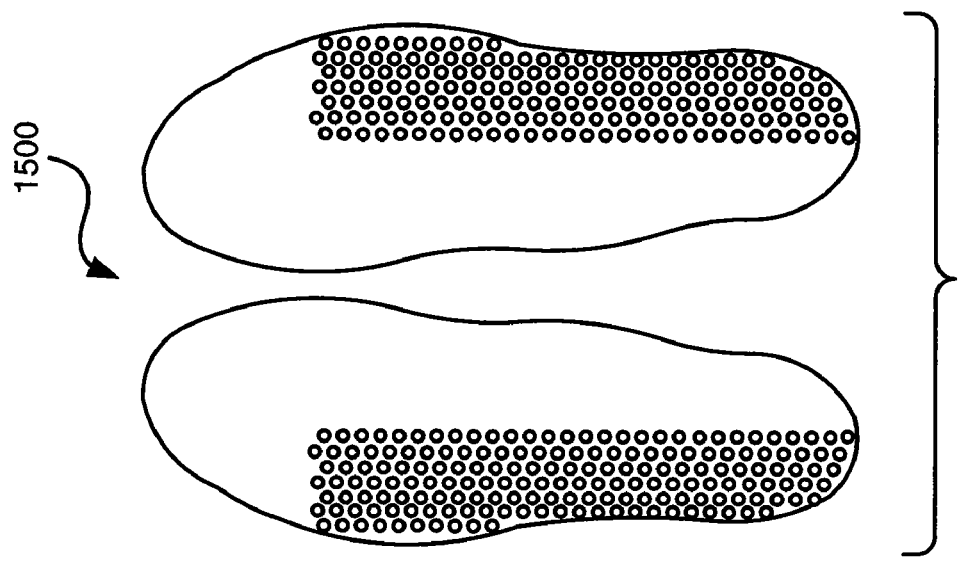
Figure 15G:
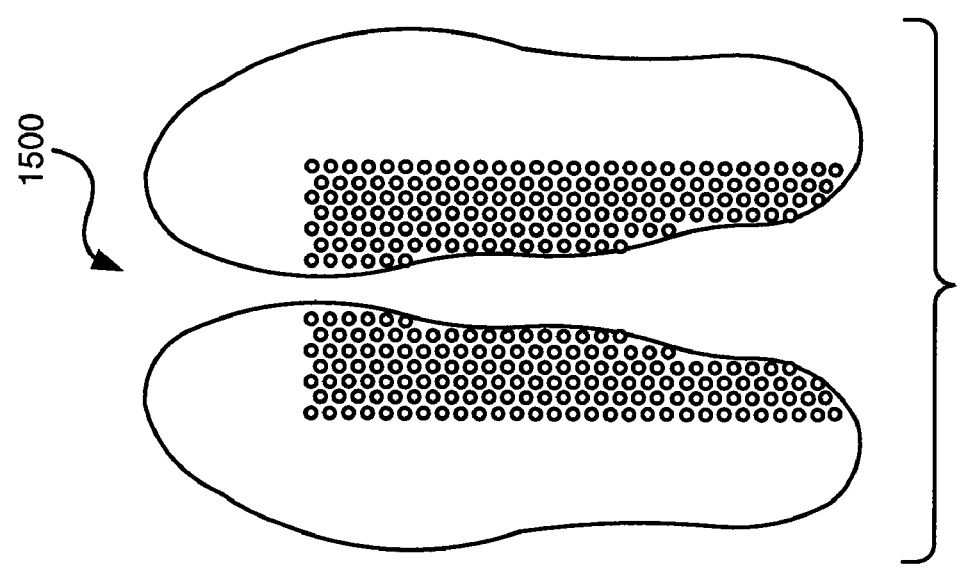
Figure 15I:
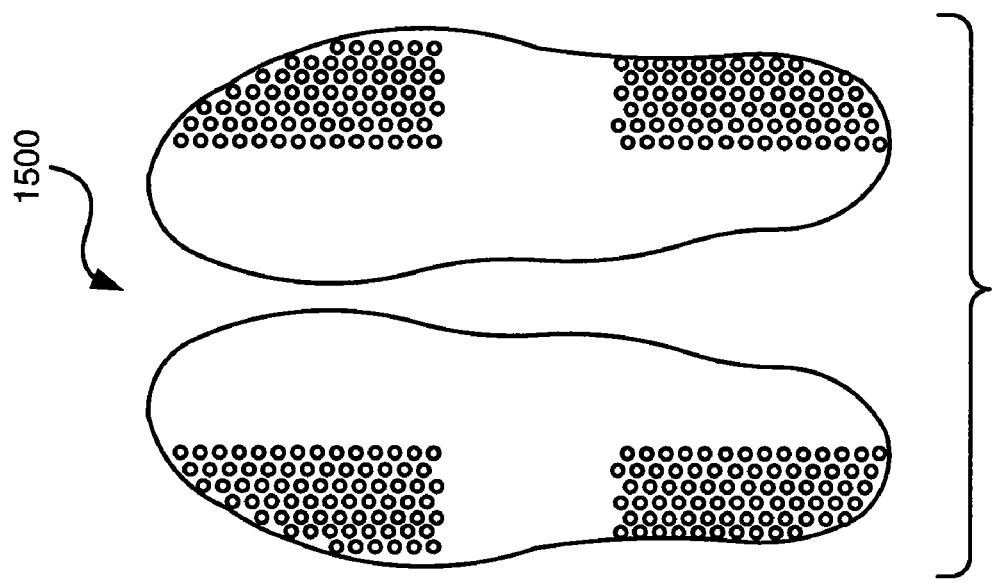
Figure 15J:
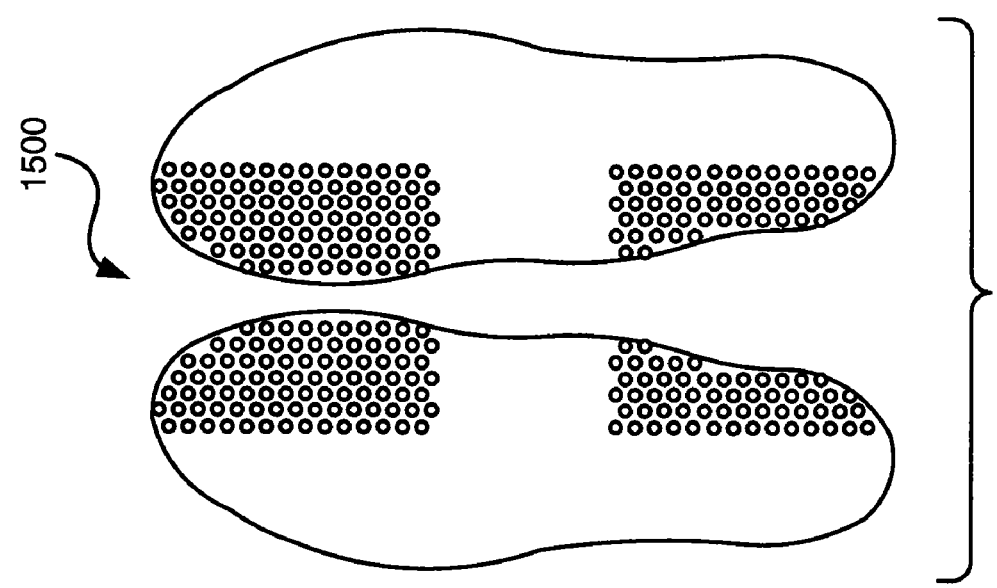
Figure 15K:
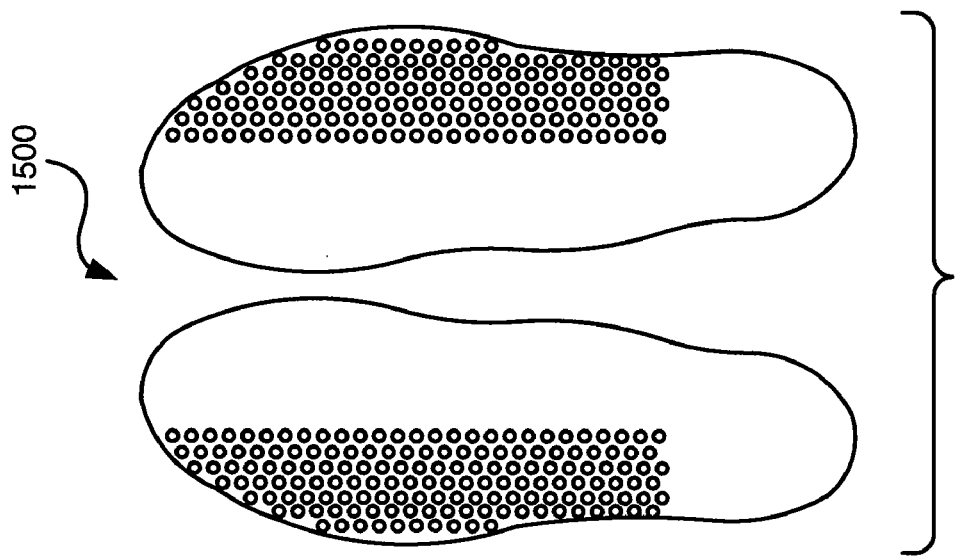
Figure 15L:
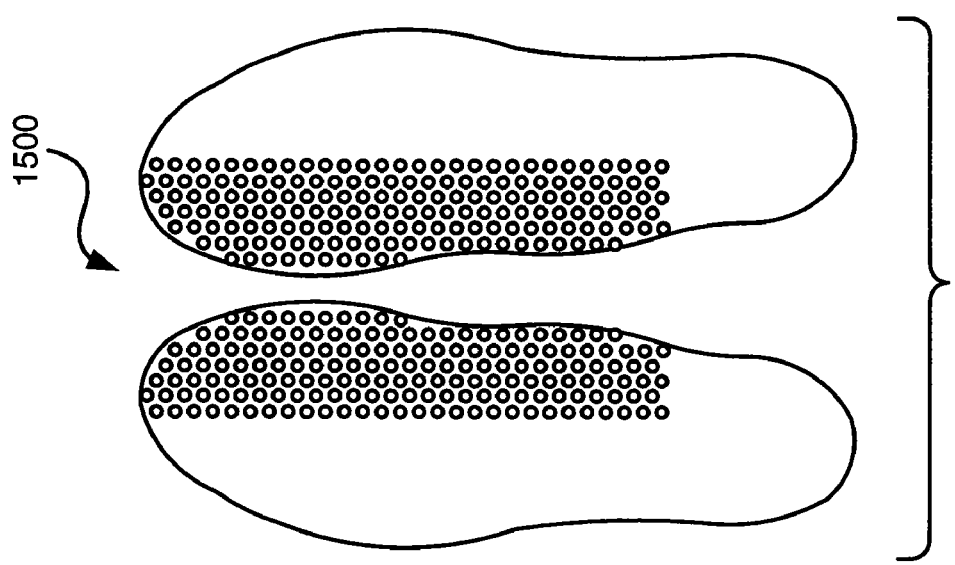
Figure 15N:
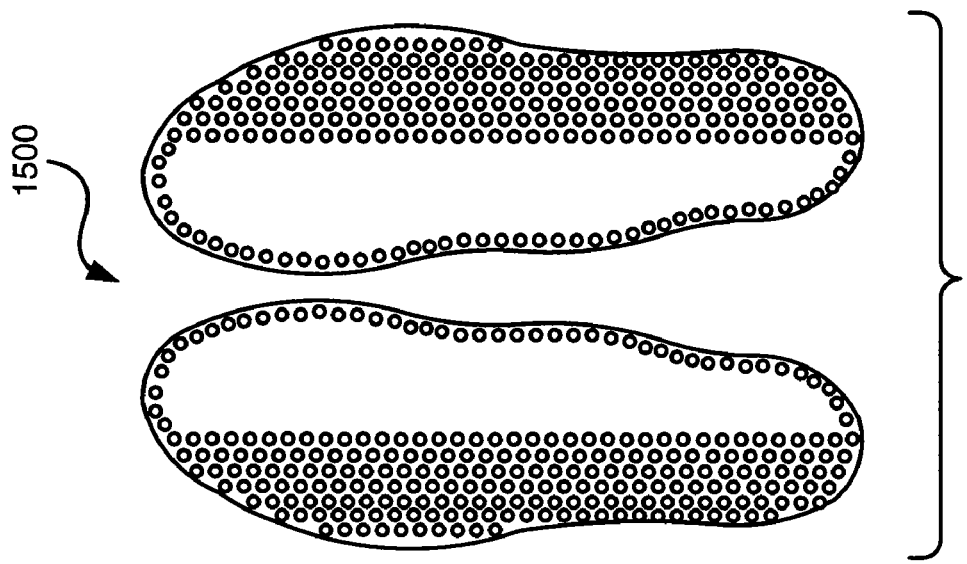

FIGS. 15A through 15N illustrate various example arrangements of footbeds 1500 that include texturing elements at various locations or regions in accordance with examples of this invention. In the footbed 1500 of FIG. 15A, the texturing elements are provided in the medial forefoot portion of the footbed 1500. In the footbed 1500 of FIG. 15B, the texturing elements are provided in the lateral forefoot portion of the footbed 1500. In the footbed 1500 of FIG. 15C, the texturing elements are provided in the medial midfoot or arch portion of the footbed 1500. In the footbed 1500 of FIG. 15D, the texturing elements are provided in the lateral midfoot or arch portion of the footbed 1500. In the footbed 1500 of FIG. 15E, the texturing elements are provided in the medial heel or rearfoot portion of the footbed 1500. In the footbed 1500 of FIG. 15F, the texturing elements are provided in the lateral heel or rearfoot portion of the footbed 1500. In the footbed 1500 of FIG. 15G, the texturing elements are provided in the medial heel and arch portions of the footbed 1500. In the footbed 1500 of FIG. 15H, the texturing elements are provided in the lateral heel and arch portions of the footbed 1500. In the footbed 1500 of FIG. 15I, the texturing elements are provided in the medial heel and forefoot portions of the footbed 1500 (with a smooth medial midfoot portion). In the footbed 1500 of FIG. 15J, the texturing elements are provided in the lateral heel and forefoot portions of the footbed 1500 (with a smooth medial midfoot portion). In the footbed 1500 of FIG. 15K, the texturing elements are provided in the medial arch and forefoot portions of the footbed 1500. In the footbed 1500 of FIG. 15L, the texturing elements are provided in the lateral arch and forefoot portions of the footbed 1500.

Figure 15M:
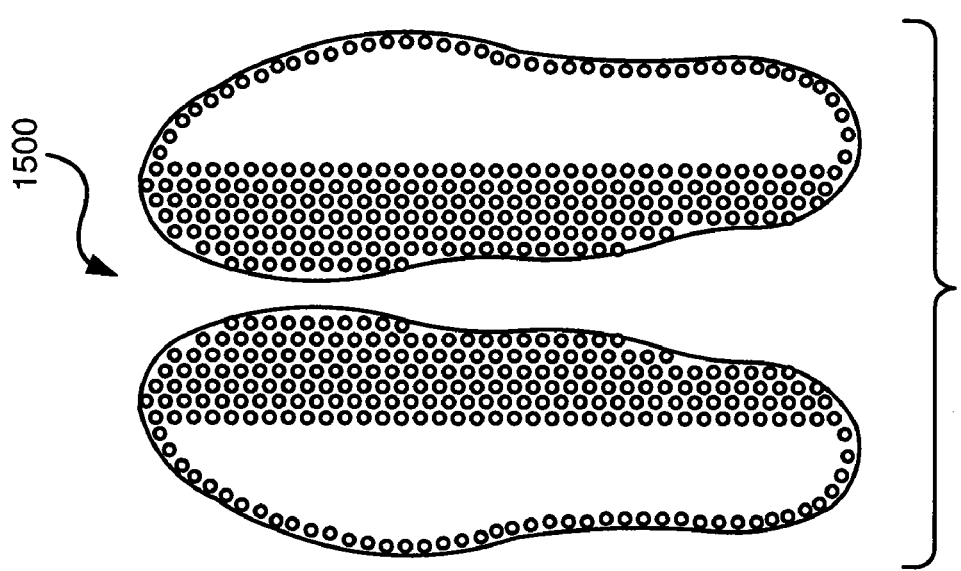

FIGS. 15M and 15N illustrate examples of footbed arrangements 1500 in which some texturing elements are provided on both the lateral and medial sides of the footbed 1500, although at least one side (e.g., the medial or lateral) of the footbed is predominantly smooth (or even substantially smooth) and the opposite side is predominantly textured (or even substantially textured). The features of FIGS. 15M and 15N (including some texturing on both sides of the footbed 1500) also may be used in conjunction with any of the example footbed structures described above.

f course, wide variations in combinations of textured area patterns, locations, regions, structures, and the like may be used without departing from this invention. Also, while FIGS. 15A through 15N generally show the left and right footbeds as mirror images of one another, this is not a requirement. Rather, if desired, different texturing patterns, locations, regions, structures, and the like may be provided on one footbed of a pair as compared to the other. Also, if desired, one footbed of a pair may contain no texturing while the other footbed contains texturing.

III. Conclusion

While the invention has been described with respect to specific examples including presently preferred modes of carrying out the invention, those skilled in the art will appreciate that there are numerous variations and permutations of the above described systems and methods. For example various aspects of the invention may be used in different combinations and various different subcombinations of aspects of the invention may be used together in a single system or method without departing from the invention. Also, various method steps described above may be changed, changed in order, omitted, and/or additional steps may be added without departing from this invention. Thus, the invention should be construed broadly as set forth in the appended claims.

The invention claimed is:

1. An article of footwear, comprising:
an upper member;
a sole structure engaged with the upper member; and
a footbed for supporting a plantar surface of a user's foot located between the upper member and the sole structure, wherein the footbed is structured in one of the following manners: (a) wherein an entire lateral side of the footbed is smooth and at least a forefoot portion of a medial side of the footbed includes plural raised areas defining a textured surface, or (b) wherein an entire medial side of the footbed is smooth and at least a forefoot portion of a lateral side of the footbed includes plural areas defining a textured surface.

2. An article of footwear according to claim 1, wherein the footbed is included as part of an insole member.

3. An article of footwear according to claim 1, wherein the footbed is included as part of a sock liner.

4. An article of footwear according to claim 1, wherein the footbed constitutes a portion of the sole structure.

5. An article of footwear according to claim 1, wherein the footbed is sized so as to substantially correspond to a foot-engaging surface of a foot-receiving chamber of the article of footwear, wherein the textured surface predominantly covers a medial half of the footbed.

6. An article of footwear according to claim 5, wherein the textured surface substantially covers the medial half of the footbed.

7. An article of footwear according to claim 1, wherein the footbed is sized so as to substantially correspond to a foot-engaging surface of a foot-receiving chamber of the article of footwear, wherein the textured surface predominantly covers a lateral half of the footbed.

8. An article of footwear according to claim 7, wherein the textured surface substantially covers the lateral half of the footbed.

9. A footbed, comprising:
a first major surface for supporting at least a substantial portion of a plantar surface of a user's foot, the first major surface including a lateral side and a medial side; and
a second major surface opposite the first major surface,
wherein the footbed is structured in one of the following manners: (a) at least one of at least a forefoot portion of the first major surface or at least a forefoot portion of the second major surface includes plural texturing members such that when a plantar surface of a user's foot applies a substantially vertical force to the footbed, the entire lateral side is smooth at the planar surface and at least a predominant portion of the medial side is textured at the plantar surface, or (b) at least one of at least a forefoot portion of the first major surface or at least a forefoot portion of the second major surface includes plural texturing members such that when a plantar surface of a user's foot applies a substantially vertical force to the footbed, the entire medial side is smooth at the plantar surface and at least a predominant portion of the lateral side is textured at the plantar surface.

10. A footbed according to claim 9, wherein the footbed constitutes an insole member.

11. A footbed according to claim 9, wherein the footbed constitutes a sock liner.

12. A footbed according to claim 9, wherein at least a substantial portion of the medial side feels textured at the plantar surface.

13. A footbed according to claim 9, wherein at least a substantial portion of the lateral side feels textured at the plantar surface.

14. A method of making an article of footwear, comprising:
engaging an upper member with a sole structure; and
providing a footbed for supporting a plantar surface of a user's foot with at least one of the upper member and the sole structure, wherein the footbed is structured in one of the following manners: (a) wherein an entire lateral side of the footbed is smooth and at least a forefoot portion of a medial side of the footbed includes plural raised areas defining a textured surface, or (b) wherein an entire medial side of the footbed is smooth and at least a forefoot portion of a lateral side of the footbed includes plural raised areas defining a textured surface.

15. A method according to claim 14, wherein the providing includes providing the footbed as at least part of an insole member.

16. A method according to claim 14, wherein the providing includes providing the footbed as at least part of a sock liner.

17. A method according to claim 14, wherein the footbed is provided as a portion of the sole structure.

18. A method according to claim 14, wherein the providing includes inserting a structure including the footbed into a foot-receiving chamber defined by at least one of the upper member or the sole structure.

19. A method according to claim 14, wherein the footbed is sized so as to substantially correspond to a foot-engaging surface of the article of footwear, and wherein the textured surface predominantly covers a medial half of the footbed.

20. A method according to claim 19, wherein the textured surface substantially covers the medial half of the footbed.

21. A method according to claim 14, wherein the footbed is sized so as to substantially correspond to a foot-engaging surface of the article of footwear, and wherein the textured surface predominantly covers a lateral half of the footbed.

22. A method according to claim 21, wherein the textured surface substantially covers the lateral half of the footbed.

* * * * *